US010485879B2

(12) United States Patent
Arya et al.

(10) Patent No.: US 10,485,879 B2
(45) Date of Patent: Nov. 26, 2019

(54) PLASMA CELL CYTOKINE VEHICLE CONTAINING FUSION PROTEINS FOR TARGETED INTRODUCTION OF SIRNA INTO CELLS AND TISSUES

(71) Applicants: The United States of America, as represented by the Secretary, Department of Health & Human Services, Rockville, MD (US); SIRNAX, INC., Ann Arbor, MI (US)

(72) Inventors: Bira Arya, Elliott City, MD (US); Michael R. Simon, Ann Arbor, MI (US)

(73) Assignees: Government Of The United States Of America As Represented By The Secretary Of The Department Of Health And Human Services, National Institutes Of Health, Washington, DC (US); Michael R. Simon, Ann Arbor, MI (US)

( * ) Notice: Subject to any disclaimer, the term of this patent is extended or adjusted under 35 U.S.C. 154(b) by 0 days.

(21) Appl. No.: 16/011,263

(22) Filed: Jun. 18, 2018

(65) Prior Publication Data

US 2018/0280526 A1 Oct. 4, 2018

Related U.S. Application Data

(60) Continuation-in-part of application No. 15/204,789, filed on Jul. 7, 2016, which is a division of application No. 14/220,726, filed on Mar. 20, 2014, now Pat. No. 9,415,116, which is a continuation of application No. 12/988,148, filed as application No. PCT/US2009/040607 on Apr. 15, 2009, now Pat. No. 8,703,921.

(60) Provisional application No. 61/045,088, filed on Apr. 15, 2008.

(51) Int. Cl.

| | |
|---|---|
| ***A61K 39/00*** | (2006.01) |
| ***A61K 47/64*** | (2017.01) |
| ***C07K 14/52*** | (2006.01) |
| ***C07K 14/005*** | (2006.01) |
| ***A61K 31/713*** | (2006.01) |
| ***C12N 15/87*** | (2006.01) |

(52) U.S. Cl.

CPC ............ *A61K 47/64* (2017.08); *A61K 31/713* (2013.01); *A61K 47/642* (2017.08); *A61K 47/6455* (2017.08); *C07K 14/005* (2013.01); *C07K 14/523* (2013.01); *C12N 15/87* (2013.01); *C07K 2319/10* (2013.01); *C07K 2319/33* (2013.01); *C07K 2319/74* (2013.01); *C07K 2319/85* (2013.01)

(58) Field of Classification Search

None

See application file for complete search history.

(56) References Cited

U.S. PATENT DOCUMENTS

| | | | |
|---|---|---|---|
| 5,108,921 | A | 4/1992 | Low et al. |
| 5,416,016 | A | 5/1995 | Low et al. |
| 5,514,548 | A | 5/1996 | Krebber et al. |
| 5,849,902 | A | 12/1998 | Arrow et al. |
| 5,898,031 | A | 4/1999 | Crooke |
| 6,107,094 | A | 8/2000 | Crooke |
| 6,172,208 | B1 | 1/2001 | Cook |
| 6,294,353 | B1 | 9/2001 | Pack et al. |
| 6,335,434 | B1 | 1/2002 | Guzaev et al. |
| 6,653,068 | B2 | 11/2003 | Frisch et al. |
| 6,667,150 | B1 | 12/2003 | Rudert et al. |
| 6,692,935 | B1 | 2/2004 | Pack et al. |
| 6,696,245 | B2 | 2/2004 | Winter et al. |
| 6,753,136 | B2 | 6/2004 | Lohning |
| 2004/0058886 | A1 | 3/2004 | Scaringe |
| 2007/0042983 | A1 | 2/2007 | Haeberli et al. |
| 2007/0231392 | A1 | 10/2007 | Wagner et al. |
| 2014/0377179 | A1 | 12/2014 | Arya et al. |

FOREIGN PATENT DOCUMENTS

| | | | | |
|---|---|---|---|---|
| WO | 0053722 | A2 | 9/2000 | |
| WO | 0214478 | A2 | 2/2002 | |
| WO | 2004110375 | A2 | 12/2004 | |
| WO | 2006023491 | A2 | 3/2006 | |
| WO | WO-2006023491 | A2 * | 3/2006 | ............. C07K 14/46 |
| WO | 2007041364 | A2 | 4/2007 | |
| WO | 2007127219 | A2 | 11/2007 | |
| WO | 2008092081 | A2 | 7/2008 | |

OTHER PUBLICATIONS

Danilova et al (Mucosa Immunology, 2015, vol. 8, No. 1 pp. 107-114). (Year: 2015).*

Caron et al (Biochemical and Biophysical Research Communications, 2004, vol. 319, pages (Year: 2004).*

Tabara, H. et al, "The dsRNA Binding Protein RDE-4 Interacts with RDE-1, DCR-1, and a DExH-Box Helicase to Direct RNAi in C. elegans", Cell, Jun. 28, 2002, pp. 861-871, vol. 109, © 2002 by Cell Press.

Zhang, H. et al., "Human Dicer preferentially cleaves dsRNAs at their termini without a requirement for ATP", The EMBO Journal, 2002, pp. 5875-5885, vol. 21, No. 21, © 2002 European Molecular Biology Organization.

(Continued)

*Primary Examiner* — Celine X Qian

(74) *Attorney, Agent, or Firm* — Avery N. Goldstein; Blue Filament Law PLLC

(57) ABSTRACT

A fusion molecule is provided that includes one or more inhibitory nucleic acids, a targeting polypeptide, and a nucleic acid binding moiety. The targeting polypeptide and the nucleic acid binding moiety include specific the amino acid sequences. A fusion molecule is also provided that includes one or more inhibitory nucleic acids, a targeting polypeptide, and a nucleic acid binding moiety adapted to bind a double-stranded RNA or to a small hairpin RNA. The targeting polypeptide being CCL27 or CCL11 or a fragment thereof.

6 Claims, 1 Drawing Sheet

Specification includes a Sequence Listing.

(56) References Cited

OTHER PUBLICATIONS

Hutvagner, G. et al., "A microRNA in a Multiple-Turnover RNAi Enzyme Complex", Science, Sep. 20, 2002, pp. 2056-2060, vol. 297, © 2002 by the American Association for the Advancement of Science; DOI: 10.1126/science.1073827.
Hutvagner, G. et al., "RNAi: nature abhors a double-strand", Current Opinion in Genetics & Development, 2002, pp. 225-232, vol. 12, © 2002 Elsevier Science Ltd.
Gortz, A. et al., "The Chemokine ESkine/CCL27 Displays Novel Modes of Intracrine and Paracrine Function", The Journal of Immunology, 2002, pp. 1387-1394, vol. 169, © 2002 by The American Association of Immunologists, Inc.; DOI: 10.4049/jimmunol.169.3.1387.
Peitz, M. et al., "Ability of the hydrophobic FGF and basic TAT peptides to promote cellular uptake of recombinant Cre recombinase: A tool for efficient genetic engineering of mammalian genomes", PNAS, Apr. 2, 2002, pp. 4489-4494, vol. 99, No. 7; DOI: 10.1073?pnas.03206869.
Diallo, M. et al., "Long Endogenous dsRNAs Can Induce Complete Gene Silencing in Mammalian Cells and Primary Cultures", Oligonucleotides, 2003, pp. 381-392, vol. 13, © 2003 Mary Ann Liebert, Inc.
Futaki, S. et al., "Membrane permeability commonly shared among arginine-rich peptides", Journal of Molecular Recognition, 2003, pp. 260-264, vol. 16, © 2003 John Wiley & Sons, Ltd.; DOI: 10.1002/jmr.635.
Mie, M. et al., "Intracellular delivery of antibodies using TAT fusion protein A", Biochemical and Biophysical Research Communications, 2003, pp. 730-734, vol. 310, © 2003 Elsevier Inc.; DOI: 10.1016/j.bbrc.2003.09.071.
Miller, V.M. et al., "Allele-specific silencing of dominant disease genes", PNAS, Jun. 10, 2003, pp. 7195-7200, vol. 100, No. 12; DOI: 10.1073?pnas.1231012100.
Van Koningsbruggen, S. et al., "Llama-derived phage display antibodies in the dissection of the human disease oculopharyngeal muscular dystrophy", Journal of Immunological Methods, 2003, pp. 149-161, vol. 279, © 2003 Elsevier B.V.; DOI: 10.1016/S0022-1759(03)00232-1.
Miyagishi, M. et al., "Strategies for Generation of an siRNA Expression Library Directed Against the Human Genome", Oligonucleotides, 2003, pp. 325-333, vol. 13, © 2003 Mary Ann Liebert, Inc.
Myers, J.W. et al., "Recombinant Dicer efficiently converts large dsRNAs into siRNAs suitable for gene silencing", Nature Biotechnology, Mar. 2003 (Published online: Feb. 18, 2003), pp. 324-328, vol. 21, © 2003 Nature Publishing Group; DOI: 10.1038/nbt792.
Caron, A. et al., "Human FGF-1 gene transfer promotes the formation of collateral vessels and arterioles in schemic muscles of hypercholesterolemic hamsters", The Journal of Gene Medicine, 2004 (Published online: Apr. 26, 2004), pp. 1033-1045, vol. 6, © 2004 John Wiley & Sons, Ltd.; DOI: 10.1002/jgm.594.
Chiu, Y.-L. et al., "Inhibition of Human Immunodeficiency Virus Type 1 Replication by RNA Interference Directed against Human Transcription Elongation Factor P-TEFb (CDK9/CyclinT1)", Journal of Virology, Mar. 2004, pp. 2517-2529, vol. 78, No. 5, © 2004 American Society for Microbiology; DOI: 10.1128/JVI.78.5.2517-2529.2004.
He, T.-C., "Adenoviral Vectors", Current Protocols in Human Genetics, 2004, pp. 12.4.1-12.4.25, Unit 12.4, Supplement 40, © 2004 by John Wiley & Sons, Inc.
Muratovska, A. et al., "Conjugate for e/cient delivery of short interfering RNA (siRNA) into mammalian cells", FEBS Letters, 2004 (Published online: Jan. 13, 2004), pp. 63-68, vol. 558, © 2004 Federation of European Biochemical Societies; DOI: 10.1016/S0014-5793(03)01505-9.
Liu, G. et al., "Small interference RNA modulation of IL-10 in human monocyte-derived dendritic cells enhances the Th1 response", Eur. J. Immunol., 2004, pp. 1680-1687, vol. 34, © 2004 WILEY-VCH Verlag GmbH & Co. KGaA, Weinheim; DOI 10.1002/eji.200425081.
Song, E. et al., "Antibody mediated in vivo delivery of small interfering RNAs via cell-surface receptors", Nature Biotechnology, Jun. 2005, pp. 709-717, vol. 23, No. 6, © 2005 Nature Publishing Group; DOI: 10.1038/nbt1101.
Rossi, J.J., "Receptor-targeted siRNAs", Nature Biotechnology, Jun. 2005, pp. 682-684, vol. 23, No. 6, © 2005 Nature Publishing Group; DOI: 10.1038/nbt0605-682.
Kumar, P. et al., "Transvascular delivery of small interfering RNA to the central nervous system", Nature, Jul. 5, 2007, pp. 39-45, vol. 448, © 2007 Nature Publishing Group; DOI: 10.1038/nature05901.
Cesarone, G. et al., "Insulin Receptor Substrate 1 Knockdown in Human MCF7 Er+ Breast Cancer Cells by Nuclease-Resistant IRS1 siRNA Conjugated to a Disulfide-Bridged D-Peptide Analogue of Insulin-Like Growth Factor 1", Bioconjugate Chem., 2007 (Published online: Oct. 9, 2007), pp. 1831-1840, vol. 18, © 2007 American Chemical Society; DOI: 10.1021/bc070135v.
Xia, C.-F. et al., "Intravenous siRNA of Brain Cancer with Receptor Targeting and Avidin-Biotin Technology", Pharmaceutical Research, Dec. 2007 (Published online: Oct. 11, 2007), pp. 2309-2316, vol. 24, No. 12, © 2007 Springer Science + Business Media, LLC; DOI: 10.1007/s11095-007-9460-8.
Bauer, S. et al., "Proteinase 3 and CD177 are expressed on the plasma membrane of the same subset of neutrophils", Journal of Leukocyte Biology, Feb. 2007, pp. 458-464, vol. 81, © 2007 Society for Leukocyte Biology; DOI: 10.1189/jlb.0806514.
Scott, L.M. et al., "JAK2 Exon 12 Mutations in Polycythemia Vera and Idiopathic Erythrocytosis", New England Journal of Medicine, Feb. 1, 2007, pp. 459-468, vol. 356, No. 5, Author manuscript available in PMC: May 20, 2010, © 2007 Massachusetts Medical Society; DOI: 10.1056/NEJMoa065202.
Forssmann, U. et al., "Inhibition of CD26/Dipeptidyl Peptidase IV Enhances CCL11/Eotaxin-Mediated Recruitment of Eosinophils In Vivo", The Journal of Immunology, 2008, pp. 1120-1127, vol. 181, © 2008 by The American Association of Immunologists, Inc.; DOI: 10.4049/jimmunol.181.2.1120.
Kumar, P. et al., "T Cell-Specific siRNA Delivery Suppresses HIV-1 Infection in Humanized Mice", Cell, Aug. 22, 2008, pp. 577-586, vol. 134, No. 4, Author manuscript available in PMC: Sep. 21, 2010; DOI: 10.1016/j.cell.2008.06.034.
Stein, D. et al., "A Specificity Comparison of Four Antisense Types: Morpholino, 2'-0-Methyl RNA, DNA, and Phosphorothioate DNA", Antisense & Nucleic Acid Drug Development, 1997, pp. 151-157, vol. 7, © 1997 Mary Ann Liebert, Inc.
International Search Report dated Nov. 2, 2010 for International Application No. PCT/US2009/040607 filed Apr. 15, 2009.
English Translation of Notification of Reasons for Refusal dated Dec. 20, 2013 for Japanese Application No. 2011-505154 filed Apr. 15, 2009.
Patent Examination Report No. 1 dated Feb. 19, 2014 for Australian Application No. 2009236270 filed Apr. 15, 2009.
English Translation of Notification of Reasons for Refusal dated Jan. 14, 2016 for Japanese Application No. 2014-250963 filed Apr. 15, 2009.
Godwin, H.A. et al., "The Synthesis of Biologically Active Pteroyloligo-γ-L-Glutamates (Folic Acid Conjugates)", The Journal of Biological Chemistry, Apr. 25, 1972, pp. 2266-2271, vol. 247, No. 8.
Grunstein, M. et al., "Colony hybridization: a method for the isolation of cloned DNAs that contain a specific gene", Proc. Nat. Acad. Sci., Oct. 1975, pp. 3961-3965, vol. 72, No. 10.
Benton, W.D. et al., "Screening Lambdagt Recombinant Clones by Hybridization to Single Plaques in situ", Science, 1977, pp. 180-182, vol. 196.
Kimmel, A.R., "Identification and Characterization of Specific Clones: Strategy for Confirming the Validity of Presumptive Clones", Methods in Enzymology, 1987, pp. 507-511, vol. 152, © 1987 by Academic Press, Inc.
Wahl, G.M. et al., "Molecular Hybridization of Immobilized Nucleic Acids: Theoretical Concepts and Practical Considerations", Methods in Enzymology, 1987, pp. 399-407, vol. 152, © 1987 by Academic Press, Inc.

(56) References Cited

OTHER PUBLICATIONS

Jacobs, B.L. et al., "Histone Proteins Inhibit Activation of the Interferon-induced Protein Kinase by Binding to Double-Stranded RnA", Journal of Interferon Research, 1988, pp. 821-830, vol. 8.

Matsuda, K. et al., "DNA-Binding Activity of Hepatitis B e Antigen Polypeptide Lacking the Protaminelike Sequence of Nucleocapsid Protein of Human Hepatitis B Virus", Journal of Virology, Sep. 1988, pp. 3517-3521, vol. 62, No. 9, © 1988, American Society for Microbiology.

St. Johnston, D. et al., "A conserved double-stranded RNA-binding domain", Proc. Natl. Acad. Sci., Nov. 1992, pp. 10979-10983, vol. 89.

Anderson, D.C. et al., "Tumor Cell Retention of Antibody Fab Fragments is Enhanced by an Attached HIV TAT Protein-Derived Peptide", Biochemical and Biophysical Research Communications, Jul. 30, 1993, pp. 876-884, vol. 194, No. 2, © 1993 by Academic Press, Inc.

Stura, E.A. et al., "Crystallization of Antibodies and Antibody-Antigen Complexes", Immunomethods, 1993, pp. 164-179, vol. 3, © 1993 by Academic Press, Inc.

Stein, C.A. et al., "Antisense Oligonucleotides as Therapeutic Agents—Is the Bullet Really Magical?", Science, Aug. 20, 1993, pp. 1004-1012, vol. 261.

Ede, N.J. et al., "Routine Preparation of Thiol Oligonucleotides: Application to the Synthesis of Oligonucleotide-Peptide Hybrids", Bioconjugate Chem., 1994, pp. 373-378, vol. 5, No. 4, © 1994 American Chemical Society.

Loetscher, P. et al., "Monocyte chemotactic proteins MCP-1, MCP-2, and MCP-3 are major attractants for human CD4+ and CD8+ T lymphocytes", The FASEB Journal, Oct. 1994, pp. 1055-1060, vol. 8, © 1994 FASEB.

Ishiwata, H. et al., "Physical-Chemistry Characteristics and Biodistribution of Poly(ethylene glycol)-Coated Liposomes Using Poly(oxyethylene) Cholesteryl Ether", Chem. Pharm. Bull., Jun. 1995, pp. 1005-1011, vol. 43, No. 6, © 1995 Pharmaceutical Society of Japan.

Lasic, D.D. et al., "Liposomes Revisited", Science, Mar. 3, 1995, pp. 1275-1276, vol. 267.

Lasic, D.D. et al., "The "Stealth" Liposome: A Prototypical Biomaterial", Chemical Reviews, Dec. 1995, pp. 2601-2628, vol. 95, No. 8, © 1995 American Chemical Society.

Liu, Y. et al., "Cationic Liposome-mediated Intravenous Gene Delivery", The Journal of Biological Chemistry, Oct. 20, 1995, pp. 24864-24870, vol. 270, No. 42, © 1995 by The American Society for Biochemistry and Molecular Biology, Inc; DOI: 10.1074/jbc270.42.24864.

Oku, N. et al., "Real-time analysis of liposomal trafficking in tumor-bearing mice by use of positron emission tomography", Biochimica et Biophysica Acta, 1995, pp. 86-90, vol. 1238, © 1995 Elsevier Science B.V.

Clemens, M.J. et al., "The Double-Stranded RNA-Dependent Protein Kinase PKR: Structure and Function", Journal of Interferon and Cytokine Research, 1997, pp. 503-524, vol. 17.

Crooke, S.T., "Advances in Understanding the Pharmacological Properties of Antisense Oligonucleotides", Advances in Pharmacology, 1997, pp. 1-49, vol. 40, © 1997 by Academic Press.

Delihas, N. et al., "Natural antisense RNA/target RNA interactions: Possible models for antisense oligonucleotide drug design", Nature Biotechnology, Aug. 1997, pp. 751-753, vol. 15, © 1997 Nature Publishing Group.

Yaneva, J. et al., "The major chromatin protein histone H1 binds preferentially to cis-platinum-damaged DNA", Proc. Natl. Acad. Sci., Dec. 1997, pp. 13448-13451, vol. 94, © 1997 by The National Academy of Sciences.

Fire, A. et al., "Potent and specific genetic interference by double-stranded RNA in Caenorhabditis elegans", Nature, Feb. 1998, pp. 806-811, vol. 391, © 1998 Nature Publishing Group.

Crooke, S.T., "Antisense Therapeutics", Biotechnology and Genetic Engineering Reviews, Apr. 1998, pp. 121-157, vol. 15; DOI: 10.1080/02648725.1998.10647954.

Habus, I. et al., "A Mild and Efficient Solid-Support Synthesis of Novel Oligonucleotide Conjugates", Bioconjugate Chem., 1998 (Published online: Feb. 5, 1998), pp. 283-291, vol. 9, No. 2, © 1998 American Chemical Society.

Funaro, A. et al., "CD38 Functions are Regulated Through an Internalization Step", The Journal of Immunology, 1998, pp. 2238-2247, vol. 160, © 1998 by The American Association of Immunologists.

Bahramian, M.B. et al., "Transcriptional and Posttranscriptional Silencing of Rodent alpha1(I) Collagen by a Homologous Transcriptionally Self-Silenced Transgene", Molecular and Cellular Biology, Jan. 1999, pp. 274-283, vol. 19, No. 1, © 1999 American Society for Microbiology.

Conry, R.M. et al., "Phase I Trial of a Recombinant Vaccinia Virus Encoding Carcinoembryonic Antigen in Metastatic Adenocarcinoma: Comparison of Intradermal versus Subcutaneous Administration", Clinical Cancer Research, Sep. 1999, pp. 2330-2337, vol. 5, © 1999 American Association for Cancer Research.

Fire, A. et al., "RNA-triggered gene silencing", Trends Genet., Sep. 1999, pp. 358-363, vol. 15, No. 9, © 1999 Elsevier Science Ltd.

Hamilton, A.J. et al., "A Species of Small Antisense RNA in Posttranscriptional Gene Silencing in Plants", Science, Oct. 29, 1999, pp. 950-952, vol. 286.

Lin, R. et al., "Policing rogue genes", Nature, Nov. 11, 1999, pp. 128-129, vol. 402, © 1999 Macmillan Magazines Ltd.

Schmajuk, G. et al., "Antisense Oligonucleotides with Different Backbones: Modification of Splicing Pathways and Efficacy of Uptake", The Journal of Biological Chemistry, Jul. 30, 1999, pp. 21783-21789, vol. 274, No. 31, © 1999 by The American Society for Biochemistry and Molecular Biology, Inc.; DOI: 10.1074/jbc.274.31.21783.

Sharp, P.A., "RNAi and double-strand RNA", Genes & Development, 1999, pp. 139-141, vol. 13, © 1999 by Cold Spring Harbor Laboratory Press.

Strauss, E., "Candidate 'Gene Silencers' Found", Science, Oct. 29, 1999, p. 886, vol. 286.

Hammond, S.M. et al., "An RNA-directed nuclease mediates post-transcriptional gene silencing in *Drosophila* cells", Nature, Mar. 16, 2000, pp. 293-296, vol. 404, © 2000 Macmillan Magazines Ltd.

Wianny, F. et al., "Specific interference with gene function by double-stranded RNA in early mouse development", Nature Cell Biology, Feb. 2000, pp. 70-75, vol. 2, © 1999 Macmillan Magazines Ltd.

Crooke, S.T., "Progress in Antisense Technology: The End of the Beginning", Methods in Enzymology, 2000, pp. 3-45, vol. 313, © 1999by Academic Press.

Nomura, M. et al., "Development of an Efficient Intermediate, α-[2-(Trimethylsilyl)ethoxy]-2-N—[2-(trimethylsilyl)ethoxycarbonyl]folic Acid, for the Synthesis of Folate (γ)-Conjugates, and Its Application to the Synthesis of Folate-Nucleoside Conjugates", J. Org. Chem., 2000 (Published online: Jul. 14, 2000), pp. 5016-5021, vol. 65, No. 16, © 2000 American Chemical Society; DOI: 10.1021/jo000132a.

Zamore, P.D. et al., "RNAi: Double-Stranded RNA Directs the ATP-Dependent Cleavage of mRNA at 21 to 23 Nucleotide Intervals", Cell, Mar. 31, 2000, pp. 25-33, vol. 101, © 2000 by Cell Press.

Pan, J. et al., "Cutting Edge: A Novel Chemokine Ligand for CCR10 and CCR3 Expressed by Epithelial Cells in Mucosal Tissues", The Journal of Immunology, 2000, pp. 2943-2949, vol. 165, © 2000 by The American Association of Immunologists; DOI: 10.4049/jimmunol.165.6.2943.

Soomets, U. et al., "Deletion analogues of transportan", Biochimica et Biophysica Acta, 2000, pp. 165-176, vol. 1467, © 2000 Elsevier Science B.V.

Temerinac, S. et al., "Cloning of PRV-1, a novel member of the uPAR receptor superfamily, which is overexpressed in polycythemia rubra vera", Blood, Apr. 15, 2000, pp. 2569-2576, vol. 95, No. 8, © 2000 by The American Society of Hematology.

Jo, D. et al., "Epigenetic regulation of gene structure and function with a cell-permeable Cre recombinase", Nature Biotechnology, Oct. 2001, pp. 929-933, vol. 19, © 2001 Nature Publishing Group.

(56) References Cited

OTHER PUBLICATIONS

Pfister, M. et al., "NAD degradation and regulation of CD38 expression by human monocytes/macrophages", Eur. J. Biochem., 2001, pp. 5601-5608, vol. 268, © FEBS 2001.
Waterhouse, P.M. et al., "Gene silencing as an adaptive defence against viruses", Nature, Jun. 14, 2001, pp. 834-842, vol. 411, © 2001 Macmillan Magazines Ltd.
Adah, S.A. et al., "Chemistry and Biochemistry of 2',5'-Oligoadenylate-Based Antisense Strategy", Abstract, Current Medicinal Chemistry, 2001, pp. 1189-1212, vol. 8, © 2001 Bentham Science Publishers Ltd.
Bass, B.L., "The short answer", Nature, May 24, 2001, pp. 428-429, vol. 411, © 2001 Macmillan Magazines Ltd.
Elbashir, S.M. et al., "Duplexes of 21±nucleotide RNAs mediate RNA interference in cultured mammalian cells", Nature, May 24, 2001, pp. 494-498, vol. 411, © 2001 Macmillan Magazines Ltd.
Parrish, S. et al., "Distinct roles for RDE-1 and RDE-4 during RNA interference in Caenorhabditis elegans", RNA, 2001, pp. 1397-1402, vol. 7, © 2001 RNA Society; DOI: 10.1017.S1355838201011074.
Provost, P. et al., "Ribonuclease activity and RNA binding of recombinant human Dicer", The EMBO Journal, 2002, pp. 5864-5874, vol. 21, No. 21, © 2002 European Molecular Biology Organization.

* cited by examiner

SEQ ID NO: 5

SDGGGSGGGGSLE

SEQ ID NO: 6

DGGGSGGGGSL

SEQ ID NO: 7

GGGSGGGG

SEQ ID NO: 8

GGGGSGGGG

```
                              SEQUENCE LISTING


<160> NUMBER OF SEQ ID NOS: 21

<210> SEQ ID NO 1
<211> LENGTH: 393
<212> TYPE: DNA
<213> ORGANISM: Artificial Sequence
<220> FEATURE:
<223> OTHER INFORMATION: /note=Description of Artificial Sequence:
      Synthetic polynucleotide"

<400> SEQUENCE: 1

atggcacgag ggaccaacgt gggccgggag tgctgcctgg agtacttcaa gggagccatt      60

ccccttagaa agctgaagac gtggtaccag acatctgagg actgctccag ggatgccatc     120

gtttttgtaa ctgtgcaggg cagggccatc tgttcggacc ccaacaacaa gagagtgaag     180

aatgcagtta aatacctgca aagccttgag aggtctgatg gtggtggctc tggcggtggg     240

ggtagcctcg accgcagcca gagccgtagc cgttattacc gccagcgcca acgttctcgc     300

cgccgtcgcc gtcgcagcct cgagcgtgga tccgcagaag aacagaaact gatctcagaa     360

gaggatctgg cccaccacca tcaccatcac taa                                  393


<210> SEQ ID NO 2
<211> LENGTH: 130
<212> TYPE: PRT
<213> ORGANISM: Artificial Sequence
<220> FEATURE:
<223> OTHER INFORMATION: /note=Description of Artificial Sequence:
      Synthetic polypeptide'

<400> SEQUENCE: 2

Met Ala Arg Gly Thr Asn Val Gly Arg Glu Cys Cys Leu Glu Tyr Phe
1               5                   10                  15

Lys Gly Ala Ile Pro Leu Arg Lys Leu Lys Thr Trp Tyr Gln Thr Ser
            20                  25                  30

Glu Asp Cys Ser Arg Asp Ala Ile Val Phe Val Thr Val Gln Gly Arg
        35                  40                  45

Ala Ile Cys Ser Asp Pro Asn Asn Lys Arg Val Lys Asn Ala Val Lys
    50                  55                  60

Thr Leu Gln Ser Leu Glu Arg Ser Asp Gly Gly Gly Ser Gly Gly Gly
65                  70                  75                  80

Gly Ser Leu Asp Arg Ser Gln Ser Arg Ser Arg Tyr Tyr Arg Gln Arg
                85                  90                  95

Gln Arg Ser Arg Arg Arg Arg Arg Arg Ser Leu Glu Arg Gly Ser Ala
            100                 105                 110

Glu Glu Gln Lys Leu Ile Ser Glu Glu Asp Leu Ala His His His His
        115                 120                 125

His His
    130
```

-continued

```
<210> SEQ ID NO 3
<211> LENGTH: 366
<212> TYPE: DNA
<213> ORGANISM: Artificial Sequence
<220> FEATURE:
<223> OTHER INFORMATION: /note=Description of Artificial Sequence:
      Synthetic polynucleotide"

<400> SEQUENCE: 3

atggcacgag ggaccaacgt gggccgggag tgctgcctgg agtacttcaa gggagccatt      60

ccccttagaa agctgaagac gtggtaccag acatctgagg actgctccag ggatgccatc     120

gtttttgtaa ctgtgcaggg cagggccatc tgttcggacc ccaacaacaa gagagtgaag     180

aatgcagtta aatacctgca aagccttgag aggtctgatg gtggtggctc tggcggtggg     240

ggtagcctcg agagacgacg aggcaggtcc cctagaagaa gaactccctc gcctcgcaga     300

cgaaggtctc aatcgccgcg tcgcagaaga tctcaatctc gggtcgacca ccatcaccat     360

cactaa                                                                366


<210> SEQ ID NO 4
<211> LENGTH: 120
<212> TYPE: PRT
<213> ORGANISM: Artificial Sequence
<220> FEATURE:
<223> OTHER INFORMATION: /note=Description Synthetic polypeptide'

<400> SEQUENCE: 4

Met Arg Gly Thr Asn Val Gly Arg Glu Cys Cys Leu Glu Tyr Phe Lys
1               5                   10                  15

Gly Ala Ile Pro Leu Arg Lys Leu Lys Thr Trp Tyr Gln Thr Ser Glu
            20                  25                  30

Asp Cys Ser Arg Asp Ala Ile Trp Phe Val Thr Val Gln Gly Arg Ala
        35                  40                  45

Ile Cys Ser Asp Pro Asn Asn Lys Arg Val Lys Asn Ala Val Lys Tyr
    50                  55                  60

Leu Gln Ser Leu Glu Arg Ser Asp Gly Gly Gly Ser Gly Gly Gly Gly
65                  70                  75                  80

Ser Leu Glu Arg Arg Arg Gly Arg Ser Pro Arg Arg Arg Thr Pro Ser
                85                  90                  95

Pro Arg Arg Arg Arg Ser Gln Ser Pro Arg Arg Arg Arg Ser Gln Ser
            100                 105                 110

Arg Val Asp His His His His His
        115                 120


<210> SEQ ID NO 5
<211> LENGTH: 13
<212> TYPE: PRT
<213> ORGANISM: Artificial Sequence
<220> FEATURE:
<223> OTHER INFORMATION: /note=Description of Artificial Sequence:
      Synthetic peptide

<400> SEQUENCE: 5

Ser Asp Gly Gly Gly Ser Gly Gly Gly Gly Ser Leu Glu
1               5                   10


<210> SEQ ID NO 6
<211> LENGTH: 11
<212> TYPE: PRT
<213> ORGANISM: Artificial Sequence
<220> FEATURE:
<223> OTHER INFORMATION: /note=Description of Artificial Sequence:
```

Synthetic peptide"

<400> SEQUENCE: 6

Asp Gly Gly Gly Ser Gly Gly Gly Gly Ser Leu
1 5 10

<210> SEQ ID NO 7
<211> LENGTH: 8
<212> TYPE: PRT
<213> ORGANISM: Artificial Sequence
<220> FEATURE:
<223> OTHER INFORMATION: /note=Description of Artificial Sequence:
Synthetic peptide"

<400> SEQUENCE: 7

Gly Gly Gly Ser Gly Gly Gly Gly
1 5

<210> SEQ ID NO 8
<211> LENGTH: 9
<212> TYPE: PRT
<213> ORGANISM: Artificial Sequence
<220> FEATURE:
<223> OTHER INFORMATION: /note=Description of Artificial Sequence:
Synthetic peptide"

<400> SEQUENCE: 8

Gly Gly Gly Gly Ser Gly Gly Gly Gly
1 5

<210> SEQ ID NO 9
<211> LENGTH: 96
<212> TYPE: PRT
<213> ORGANISM: Artificial Sequence
<220> FEATURE:
<223> OTHER INFORMATION: /note=Description of Artificial Sequence:
Synthetic polypeptide'

<400> SEQUENCE: 9

Ala Arg Gly Thr Asn Val Gly Arg Glu Cys Cys Leu Glu Tyr Phe Lys
1 5 10 15

Gly Ala Ile Pro Leu Arg Lys Leu Lys Thr Trp Tyr Gln Thr Ser Glu
20 25 30

Asp Cys Ser Arg Asp Ala Ile Val Phe Val Thr Val Gln Gly Arg Ala
35 40 45

Ile Cys Ser Asp Pro Asn Asn Lys Arg Val Lys Asn Ala Val Lys Tyr
50 55 60

Leu Gln Ser Leu Glu Arg Ser Asp Gly Gly Gly Ser Gly Gly Gly Gly
65 70 75 80

Ser Pro Gly Arg Arg Arg Arg Arg Ser Gln Ser Arg Arg Arg Arg Arg
85 90 95

<210> SEQ ID NO 10
<211> LENGTH: 92
<212> TYPE: PRT
<213> ORGANISM: Artificial Sequence
<220> FEATURE:
<223> OTHER INFORMATION: /note=Description of Artificial Sequence:
Synthetic polypeptide'

<400> SEQUENCE: 10

Ser Pro Tyr Ser Ser Asp Thr Thr Pro Cys Cys Phe Ala Tyr Ile Ala
1 5 10 15

Arg Pro Leu Pro Arg Ala His Ile Lys Glu Tyr Phe Tyr Thr Ser Gly

-continued

```
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser Gly Gly Gly Ser Gly Gly Gly Gly Ser Pro Gly Arg
65                  70                  75                  80

Arg Arg Arg Arg Ser Gln Ser Arg Arg Arg Arg Arg
                85                  90


<210> SEQ ID NO 11
<211> LENGTH: 102
<212> TYPE: PRT
<213> ORGANISM: Artificial Sequence
<220> FEATURE:
<223> OTHER INFORMATION: /note=Description of Artificial Sequence:
      Synthetic polypeptide'

<400> SEQUENCE: 11

Glu Ala Pro Asp Ala Ile Asn Ala Pro Val Thr Cys Cys Tyr Asn Phe
1               5                   10                  15

Thr Asn Arg Lys Ile Ser Val Gln Arg Leu Ala Ser Tyr Arg Arg Ile
            20                  25                  30

Thr Ser Ser Lys Cys Pro Lys Glu Ala Val Ile Phe Lys Thr Ile Val
        35                  40                  45

Ala Lys Glu Ile Cys Ala Asp Pro Lys Gln Lys Trp Val Gln Asp Ser
    50                  55                  60

Met Asp His Leu Asp Lys Gln Thr Gln Thr Pro Lys Thr Gly Gly Gly
65                  70                  75                  80

Gly Ser Gly Gly Gly Gly Ser Pro Gly Arg Arg Arg Arg Arg Ser Gln
                85                  90                  95

Ser Arg Arg Arg Arg Arg
            100


<210> SEQ ID NO 12
<211> LENGTH: 15
<212> TYPE: PRT
<213> ORGANISM: Homo sapiens

<400> SEQUENCE: 12

Arg Ser Arg Arg Arg Arg Arg Arg Ser Cys Gln Thr Arg Arg Arg
1               5                   10                  15


<210> SEQ ID NO 13
<211> LENGTH: 25
<212> TYPE: RNA
<213> ORGANISM: Artificial Sequence
<220> FEATURE:
<223> OTHER INFORMATION: /note=Description of Artificial Sequence:
      Synthetic polynucleotide"

<400> SEQUENCE: 13

aggugaccag cacacugacc aucaa                                           25


<210> SEQ ID NO 14
<211> LENGTH: 25
<212> TYPE: RNA
<213> ORGANISM: Artificial Sequence
<220> FEATURE:
<223> OTHER INFORMATION: /note=Description of Artificial Sequence:
      Synthetic polynucleotide"
```

-continued

<400> SEQUENCE: 14
uugaugguca gugugcuggu caccu 25

<210> SEQ ID NO 15
<211> LENGTH: 25
<212> TYPE: RNA
<213> ORGANISM: Artificial Sequence
<220> FEATURE:
<223> OTHER INFORMATION: /note=Description of Artificial Sequence:
Synthetic polynucleotide"

<400> SEQUENCE: 15
cagcaucugc gaggaugacu ggaau 25

<210> SEQ ID NO 16
<211> LENGTH: 25
<212> TYPE: RNA
<213> ORGANISM: Artificial Sequence
<220> FEATURE:
<223> OTHER INFORMATION: /note=Description of Artificial Sequence:
Synthetic polynucleotide"

<400> SEQUENCE: 16
auuccaguca uccucgcaga ugcug 25

<210> SEQ ID NO 17
<211> LENGTH: 369
<212> TYPE: DNA
<213> ORGANISM: Artificial Sequence
<220> FEATURE:
<223> OTHER INFORMATION: /note=Description of Artificial Sequence:
Synthetic polynucleotide"

<400> SEQUENCE: 17
atggtcctac tgccacccag cactgcctgc tgtactcagc tctaccgaaa gccactctca 60
gacaagctac tgaggaaggt catccaggtg gaactgcagg aggctgacgg ggactgtcac 120
ctccgggctt tcgtgcttca cctggctcaa cgcagcatct gcatccaccc ccagaacccc 180
agcctgtcac agtggtttga gcaccaagag agaaagctcc atgggactct gcccaagctg 240
aattttggga tgctaaggaa aatgggcggt ggtggctctg gcggtgaagc ttccctcgac 300
cgcagccaga gccgtagccg ttattaccgc cagcgccaac gttctcgccg ccgtcgccgt 360
cgcagctaa 369

<210> SEQ ID NO 18
<211> LENGTH: 122
<212> TYPE: PRT
<213> ORGANISM: Artificial Sequence
<220> FEATURE:
<223> OTHER INFORMATION: /note=Description of Artificial Sequence:
Synthetic polypeptide'

<400> SEQUENCE: 18

Met Val Leu Leu Pro Pro Ser Thr Ala Cys Cys Thr Gln Leu Tyr Arg
1 5 10 15

Lys Pro Leu Ser Asp Lys Leu Leu Arg Lys Val Ile Gln Val Glu Leu
20 25 30

Gln Glu Ala Asp Gly Asp Cys His Leu Arg Ala Phe Val Leu His Leu
35 40 45

Ala Gln Arg Ser Ile Cys Ile His Pro Gln Asn Pro Ser Leu Ser Gln
50 55 60

Trp Phe Glu His Gln Glu Arg Lys Leu His Gly Thr Leu Pro Lys Leu

-continued

```
65                  70                  75                  80

Asn Phe Gly Met Leu Arg Lys Met Gly Gly Gly Gly Ser Gly Gly Glu
                85                  90                  95

Ala Ser Leu Asp Arg Ser Gln Ser Arg Ser Arg Tyr Tyr Arg Gln Arg
            100                 105                 110

Gln Arg Ser Arg Arg Arg Arg Arg Arg Ser
        115                 120


<210> SEQ ID NO 19
<211> LENGTH: 327
<212> TYPE: DNA
<213> ORGANISM: Artificial Sequence
<220> FEATURE:
<223> OTHER INFORMATION: /note=Description of Artificial Sequence:
      Synthetic polynucleotide"

<400> SEQUENCE: 19

atggggccag cttctgtccc aaccacctgc tgctttaacc tggccaatag gaagataccc      60

cttcagcgac tagagagcta caggagaatc accagtggca aatgtcccca gaaagctgtg     120

atcttcaaga ccaaactggc caaggatatc tgtgccgacc ccaagaagaa gtgggtgcag     180

gattccatga agtatctgga ccaaaaatct ccaactccaa agccaggtgg tggctctggc     240

ggtgaagctt ccctcgaccg cagccagagc cgtagccgtt attaccgcca gcgccaacgt     300

tctcgccgcc gtcgccgtcg cagctaa                                         327


<210> SEQ ID NO 20
<211> LENGTH: 108
<212> TYPE: PRT
<213> ORGANISM: Artificial Sequence
<220> FEATURE:
<223> OTHER INFORMATION: /note=Description of Artificial Sequence:
      Synthetic polypeptide'

<400> SEQUENCE: 20

Met Gly Pro Ala Ser Val Pro Thr Thr Cys Cys Phe Asn Leu Ala Asn
1               5                   10                  15

Arg Lys Ile Pro Leu Gln Arg Leu Glu Ser Tyr Arg Arg Ile Thr Ser
            20                  25                  30

Gly Lys Cys Pro Gln Lys Ala Val Ile Phe Lys Thr Lys Leu Ala Lys
        35                  40                  45

Asp Ile Cys Ala Asp Pro Lys Lys Lys Trp Val Gln Asp Ser Met Lys
    50                  55                  60

Tyr Leu Asp Gln Lys Ser Pro Thr Pro Lys Pro Gly Gly Gly Ser Gly
65                  70                  75                  80

Gly Glu Ala Ser Leu Asp Arg Ser Gln Ser Arg Ser Arg Tyr Tyr Arg
                85                  90                  95

Gln Arg Gln Arg Ser Arg Arg Arg Arg Arg Arg Ser
            100                 105


<210> SEQ ID NO 21
<211> LENGTH: 184
<212> TYPE: PRT
<213> ORGANISM: Artificial Sequence
<220> FEATURE:
<223> OTHER INFORMATION: /note=Description of Artificial Sequence:
      Synthetic polypeptide'

<400> SEQUENCE: 21

Met Gln Gln Arg Gly Leu Ala Ile Val Ala Leu Ala Val Cys Ala Ala
1               5                   10                  15
```

-continued

```
Leu His Ala Ser Glu Ala Ile Leu Pro Ile Ala Ser Ser Cys Cys Thr
            20                  25                  30

Glu Val Ser His His Ile Ser Arg Arg Leu Leu Glu Arg Val Asn Met
        35                  40                  45

Cys Arg Ile Gln Arg Ala Asp Gly Asp Cys Asp Leu Ala Ala Val Ile
    50                  55                  60

Leu His Val Lys Arg Arg Arg Ile Cys Val Ser Pro His Asn His Thr
65                  70                  75                  80

Val Lys Gln Trp Met Lys Val Gln Ala Ala Lys Lys Asn Gly Lys Gly
                85                  90                  95

Asn Val Cys His Arg Lys Lys His His Gly Lys Arg Asn Ser Asn Arg
            100                 105                 110

Ala His Gln Gly Lys His Glu Thr Tyr Gly His Lys Thr Pro Tyr Gly
        115                 120                 125

Gly Gly Ser Gly Gly Glu Ala Ser Leu Asp Arg Ser Gln Ser Arg Ser
    130                 135                 140

Arg Tyr Tyr Arg Gln Arg Gln Arg Ser Arg Arg Arg Arg Arg Arg Ser
145                 150                 155                 160

Leu Glu Arg Gly Ser Ala Glu Glu Gln Lys Leu Ile Ser Glu Glu Asp
                165                 170                 175

Leu Ala His His His His His His
            180
```

PLASMA CELL CYTOKINE VEHICLE CONTAINING FUSION PROTEINS FOR TARGETED INTRODUCTION OF SIRNA INTO CELLS AND TISSUES

RELATED APPLICATIONS

This application is a continuation-in-part of U.S. application Ser. No. 15/204,789 filed on Jul. 7, 2016 that in turn is a divisional application of U.S. application Ser. No. 14/220,726 filed on Mar. 20, 2014, now U.S. Pat. No. 9,415,116 that in turn is a continuation of U.S. application Ser. No. 12/988,148 filed Mar. 8, 2011 now U.S. Pat. No. 8,703,921 that is a U.S. national phase filing of PCT/US2009/040607 filed Apr. 15, 2009 that in turn claim the priority benefit of U.S. Provisional Application No. 61/045,088, filed on Apr. 15, 2008; the contents of the aforementioned are hereby incorporated by reference.

STATEMENT OF RIGHTS TO INVENTIONS MADE UNDER FEDERALLY SPONSORED RESEARCH

Research supporting this application was carried out by the United States of America as represented by the Secretary, Department of Health and Human Services. This research was supported by grant NCI K08118416 from the National Institute of Health. The Government may have certain rights in this invention.

FIELD OF THE INVENTION

The present invention relates in general to gene product suppression and in particular to gene product suppression through delivery of double-stranded RNA or small hairpin RNA targeting a particular protein within a subject.

BACKGROUND OF THE INVENTION

RNA interference refers to the process of sequence-specific post-transcriptional gene silencing in animals that is mediated by small inhibitory nucleic acid molecules (siRNAs) a double-stranded RNA (dsRNA) that is homologous in sequence to a portion of a targeted messenger RNA. See Fire, et al., Nature 391:806, 1998, and Hamilton, et al., Science 286:950-951, 1999. These dsRNAs serve as guide sequences for the multi-component nuclease machinery within the cell that degrade the endogenous-cognate mRNAs (i.e., mRNAs that share sequence identity with the introduced dsRNA).

The process of post-transcriptional gene silencing is thought to be an evolutionarily-conserved cellular defense mechanism used to prevent the expression of foreign genes and is commonly shared by diverse flora and fauna. Fire, et al., Trends Genet. 15:358, 1999. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

RNAi has been studied in a variety of systems. Fire et al. were the first to observe RNAi in *C. elegans*. Nature 391:806, 1998. Bahramian & Zarbl and Wianny & Goetz describe RNAi mediated by dsRNA in mammalian systems. Molecular and Cellular Biology 19:274-283, 1999, and Nature Cell Biol. 2:70, 1999, respectively. Hammond, et al., describes RNAi in *Drosophila* cells transfected with dsRNA. Nature 404:293, 2000. Elbashir, et al., describe RNAi induced by introduction of duplexes of synthetic 21-nucleotide RNAs in cultured mammalian cells including human embryonic kidney and HeLa cells. Nature 411:494, 2001.

To date, siRNA is an emerging novel field with significant clinical implications. However, the technology is hampered by a number of limitations, such as difficulty and impracticality of its delivery in vivo. Although viral vector-based siRNA delivery systems have been widely used, their specificity and safety remains significant issue. While delivery of nucleic acids offers advantages over delivery of cytotoxic proteins such as reduced toxicity prior to internalization, there is a need for high specificity of delivery, which is currently unavailable with the present systems.

The benefits of preventing specific protein production in mammals include the ability to treat disease caused by such proteins. Such diseases include those that are caused directly by such a protein such as multiple myeloma and Waldenström's macroglobulinemia which are caused by harmful concentrations of a monoclonal immunoglobulin as well as diseases in which the protein plays a contributory role such as the effects of inflammatory cytokines in asthma.

Introduction of dsRNA into mammalian cells induces an interferon response which causes a global inhibition of protein synthesis and cell death. However, dsRNA several hundred base pairs in length have been demonstrated to be able to induce specific gene silencing following cellular introduction by a DNA plasmid (Diallo M et al. Oligonucleotides 2003).

Waldenström's macroglobulinemia remains an incurable and fatal disease. The manifestations of this disease that are due to high concentrations of monoclonal IgM are hyperviscosity and systemic amyloidosis which may result in death.

Thus, there exists a need to develop a treatment for Waldenström's macroglobulinemia based on siRNA.

SUMMARY OF THE INVENTION

A fusion protein and process are provided by which double-stranded RNA containing small interfering RNA nucleotide sequences is introduced into specific cells and tissues. CCL27 and CCL11, cell surface receptor specific cytokine vehicles specific to CCR10 and CCR3 cell surface receptor specific binding sites on plasma cells, respectively, are provided. In addition CCL28, cell surface receptor specific cytokine vehicle specific to both CCR10 and CCR3 cell surface receptor specific binding sites on plasma cells, respectively, are provided (Pan J et al 2000). An RNA binding protein fused to the cytokines is adsorbed with a double-stranded RNA or to a small hairpin RNA sequence complementary to a nucleotide sequence of a target gene in the cell and includes a small interfering RNA operative to suppress production of immunoglobulins which are the target cellular proteins. The cytokines induce internalization into the plasma cells of the fusion proteins subsequent to the binding of the cytokines to the cell surface receptors of the target plasma cells (Forssmann 2008, Jarmin 2002). The symptoms of conditions of Waldenström's macroglobulinemia are so treated.

In a first aspect, the invention features a complex comprising one or more inhibitory nucleic acids and a targeting polypeptide, wherein the targeting polypeptide comprises a cell surface receptor ligand.

In one embodiment, the targeting polypeptide further comprises a nucleic acid binding moiety. In a further embodiment, the nucleic acid binding moiety comprises a nucleic acid binding domain.

In another embodiment, the nucleic acid binding domain comprises protamine, or a fragment thereof. In a related embodiment, the protamine is human protamine.

In another embodiment, the inhibitory nucleic acid is a single stranded DNA or RNA. In a further related embodiment, the inhibitory nucleic acid is a double stranded DNA or RNA. In still another related embodiment, the nucleic acid binding moiety and the targeting polypeptide are separated by a spacer peptide. In one particular embodiment, the spacer peptide comprises SEQ ID NO: 5 (SDGGGSGGGGSLE). In another particular embodiment, the spacer peptide comprises SEQ ID NO: 6: (DGGGSGGGGSL).

In another embodiment, the double stranded RNA comprises one strand that is complementary to an RNA interference target, and another strand that is identical to an RNA interference target.

In a further embodiment, the inhibitory nucleic acid is selected from the group consisting of: short interfering nucleic acid (siNA), short interfering RNA (siRNA), double-stranded RNA (dsRNA), micro-RNA (miRNA), and short hairpin RNA (shRNA).

In one embodiment, the inhibitory nucleic acids comprise at least two double stranded RNAs.

In another aspect, the invention features a complex comprising one or more inhibitory nucleic acids and a targeting polypeptide, wherein the targeting polypeptide further comprises a nucleic acid binding moiety, encoded by the nucleic acid set forth as SEQ ID NO: 1 or SEQ ID NO: 3.

In still another aspect, the invention features a complex comprising a targeting polypeptide and a nucleic acid binding moiety, encoded by a polypeptide comprising the amino acid sequence of SEQ ID NO: 2 or SEQ ID NO: 4.

In one embodiment of the above aspects, the complex further comprises an inhibitory nucleic acid.

In a related embodiment of the aspects described above, the one or more inhibitory nucleic acids and the targeting polypeptide are joined by a linker.

In another aspect, the invention features a fusion molecule comprising one or more inhibitory nucleic acids and a targeting polypeptide, wherein the targeting polypeptide comprises a cell surface receptor ligand.

In one embodiment, the targeting polypeptide further comprises a linker. In a related embodiment, the linker comprises a nucleic acid binding domain. In a further related embodiment, the nucleic acid binding domain comprises protamine, or a fragment thereof. In still another embodiment, the protamine is human protamine.

In another embodiment, the inhibitory nucleic acid is a single stranded DNA or RNA. In a further related embodiment, the inhibitory nucleic acid is a double stranded DNA or RNA. In still another related embodiment, the nucleic acid binding moiety and the targeting polypeptide are separated by a spacer peptide. In one particular embodiment, the spacer peptide comprises SEQ ID NO: 5 (SDGGGSGGGGSLE). In another particular embodiment, the spacer peptide comprises SEQ ID NO: 6: (DGGGSGGGGSL).

In another further embodiment, the spacer peptide comprises SEQ ID NO: 7 (GGGSGGGG). In another embodiment, the spacer peptide comprises SEQ ID NO: 8 (GGGGSGGGG).

In another embodiment, the double stranded RNA comprises one strand that is complementary to an RNA interference target, and another strand that is identical to an RNA interference target.

In a further embodiment, the inhibitory nucleic acid is selected from the group consisting of: short interfering nucleic acid (siNA), short interfering RNA (siRNA), double-stranded RNA (dsRNA), micro-RNA (miRNA), and short hairpin RNA (shRNA).

In one embodiment, the inhibitory nucleic acids comprise at least two double stranded RNAs.

In another aspect, the invention features a fusion molecule comprising one or more inhibitory nucleic acids and a targeting polypeptide, wherein the targeting polypeptide further comprises a nucleic acid binding moiety, encoded by the nucleic acid set forth as SEQ ID NO: 1 or SEQ ID NO: 3.

In another aspect, the invention features a fusion molecule comprising a targeting polypeptide and a nucleic acid binding moiety, encoded by a polypeptide comprising the amino acid sequence of SEQ ID NO: 2 or SEQ ID NO: 4.

In one embodiment, the fusion molecule further comprises an inhibitory nucleic acid.

In still another aspect, the invention features a method of decreasing the level of gene expression in a cell comprising: contacting the cell with a complex comprising one or more inhibitory nucleic acids that decrease the expression of one or more target genes and a targeting polypeptide, wherein the targeting polypeptide comprises a cell surface receptor ligand, thereby decreasing the level of gene expression in the cell.

In another aspect, the invention features a method of delivering inhibitory RNA molecules into a cell, the method comprising contacting the cell with a complex comprising one or more double stranded RNAs and a targeting polypeptide, wherein the targeting polypeptide comprises a cell surface receptor ligand, thereby delivering inhibitory RNA molecules into a cell.

In still another aspect, the invention features a method of treating or preventing a disease or disorder in a subject by decreasing the level of gene expression comprising: contacting the cell with a complex comprising one or more inhibitory nucleic acids that reduce the expression of one or more target genes and a targeting polypeptide, wherein the targeting polypeptide comprises a cell surface receptor ligand, thereby treating or preventing a disease or disorder in a subject.

In one embodiment, the method further comprises treatment with an additional agent. In a related embodiment, the agent is a therapeutic agent.

In still another aspect, the invention features a method of delivering one or more agents to a target cell comprising: contacting the cell with a complex comprising one or more inhibitory nucleic acids that reduce the expression of one or more target genes, wherein the one or more inhibitory nucleic acids are coupled to an agent, and a targeting polypeptide, wherein the targeting polypeptide comprises of a cell surface receptor ligand, thereby delivering the agent to a target cell.

In one embodiment, the agent is a therapeutic agent.

In another embodiment, the agent is a label.

In another aspect, the invention features a method of delivering an imaging agent into a cell in a subject comprising: contacting the cell with a complex comprising one or more inhibitory nucleic acids that reduce the expression of one or more target genes, wherein the one or more inhibitory nucleic acids are coupled to the imaging agent, and a targeting polypeptide, wherein the targeting polypeptide consists of a cell surface receptor ligand, delivering the agent into the cell.

In a further related embodiment, the nucleic acid binding domain comprises protamine, or a fragment thereof. In still another embodiment, the protamine is human protamine.

In another embodiment, the inhibitory nucleic acid is a single stranded DNA or RNA. In a further related embodiment, the inhibitory nucleic acid is a double stranded DNA or RNA. In still another related embodiment, the nucleic acid binding moiety and the targeting polypeptide are separated by a spacer peptide. In one particular embodiment, the spacer peptide comprises SEQ ID NO: 5 (SDGGGSGGGGSLE). In another particular embodiment, the spacer peptide comprises SEQ ID NO: 6: (DGGGSGGGGSL). In another embodiment, the spacer peptide comprises SEQ ID NO: 7 (GGGSGGGG). In still another embodiment, the spacer peptide comprises SEQ ID NO: 8 (GGGGSGGGG).

In another embodiment, the double stranded RNA comprises one strand that is complementary to an RNA interference target, and another strand that is identical to an RNA interference target.

In a further embodiment, the inhibitory nucleic acid is selected from the group consisting of: short interfering nucleic acid (siNA), short interfering RNA (siRNA), double-stranded RNA (dsRNA), micro-RNA (miRNA), and short hairpin RNA (shRNA).

In one embodiment, the inhibitory nucleic acids comprise at least two double stranded RNAs.

In another embodiment, the inhibitory nucleic acids further comprise an agent. In a related embodiment, the agent is a label. In another related embodiment, the label is selected from a radiolabel or a fluorescent label. In still another embodiment, the agent is a therapeutic agent.

In one embodiment of any one of the above aspects, the targeting polypeptide and the nucleic acid binding moiety are encoded by a nucleic acid sequence selected from the group consisting of: SEQ ID NO: 1 and SEQ ID NO: 3.

In another embodiment of any one of the above aspects, the cell is a cultured cell.

In another embodiment of any one of the above aspects, the cell is part of a subject animal.

In another embodiment of any one of the above aspects, the cell is selected from the group consisting of: immune cells, epithelial cells, endothelial cells, cardiac cells, neural cells, hepatocytes, lymphocytes and myocytes.

In another embodiment of any one of the above aspects, the cell is a malignant cell. In still another embodiment of any one of the above aspects, the cell is a stem cell.

In still another embodiment of any one of the above aspects, the subject is a human. In yet another embodiment of any one of the above aspects, the subject is suffering from a Waldenstrom's macroglobulinemia.

In another aspect, the invention features a pharmaceutical composition for treating or preventing a disease or disorder in a subject comprising one or more inhibitory nucleic acids and a targeting polypeptide, wherein the targeting polypeptide comprises a cell surface receptor ligand, thereby treating or preventing a disease or disorder in a subject.

In one embodiment, the targeting polypeptide and a nucleic acid binding moiety are encoded by a nucleic acid sequence selected from the group consisting of: SEQ ID NO: 1 and SEQ ID NO: 3.

In another embodiment, the pharmaceutical composition further comprises an additional agent.

In another aspect, the invention features a pharmaceutical composition for delivering one or more agents to a target cell comprising one or more inhibitory nucleic acids, wherein the one or more inhibitory nucleic acids are coupled to an agent, and a targeting polypeptide, wherein the targeting polypeptide consists of a cell surface receptor ligand, thereby treating or preventing a disease or disorder in a subject.

In one embodiment, the agent is a therapeutic agent.

In another aspect, the invention features a kit comprising the fusion molecule of any one of the aspects as described herein, and instructions for use.

BRIEF DESCRIPTION OF THE DRAWINGS

FIG. 1 shows SEQ ID NO: 5, SEQ ID NO: 6, SEQ ID NO: 7 and SEQ ID NO: 8. The sequence represented by SEQ ID NOs 5-8 corresponds to exemplary spacer sequences that separate the nucleic acid binding moiety and the targeting polypeptide.

DETAILED DESCRIPTION OF THE INVENTION

The present invention has utility in suppression of deleterious gene expression products. Production of specific proteins is associated with Waldenström's macroglobulinemia. Inventive compositions include one of a long or short dsRNA, or short hairpin RNA (shRNA) that is adsorbed to a RNA binding protein that is integrated into a scFv that includes a cell surface receptor specific ligand such that the RNA binding protein and ligand create a single protein. The ligand is targeted to a specific tissue and/or cell type upon delivery to a subject. In designing a ligand coupled dsRNA or shRNA binding protein, a target tissue and/or cell is selected, and the targeted cell type is analyzed for receptors that internalize ligands following receptor-ligand binding.

Definitions

The following definitions are provided for specific terms which are used in the following written description.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used in the specification and claims, the singular form "a", "an" and "the" include plural references unless the context clearly dictates otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. The terms "administration" or "administering" are defined to include an act of providing a compound or pharmaceutical composition of the invention to a subject in need of treatment.

The phrase "in combination with" is intended to refer to all forms of administration that provide the inhibitory nucleic acid molecule and the chemotherapeutic agent together, and can include sequential administration, in any order.

By "subject" is intended to include vertebrates, preferably a mammal. Mammals include, but are not limited to, humans.

By "cell surface receptor specific ligand" as used herein is meant to refer to a molecule that binds to a cell surface receptor or cell surface antigen. In preferred examples, a ligand is then coupled to an inhibitory nucleotide.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids. In preferred examples, the fragment is a fragment of SEQ ID NO: 1 or SEQ ID NO: 3.

By "inhibitory nucleic acid" is meant a single or double-stranded RNA, siRNA (short interfering RNA), shRNA (short hairpin RNA), or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises or corresponds to at least a portion of a target nucleic acid molecule, or an ortholog thereof, or comprises at least a portion of the complementary strand of a target nucleic acid molecule.

Nucleic acid molecules useful in the methods of the invention include a nucleic acid molecule encoding SEQ ID NO: 1 or SEQ ID NO: 3 or fragments thereof that retain binding characteristics of the native sequence. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

The term "antisense nucleic acid", as used herein, refers to a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. For a review of antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol., 40, 1-49. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

By "small molecule" inhibitor is meant a molecule of less than about 3,000 daltons having antagonist activity against a specified target.

By "RNA" is meant to include polynucleotide molecules comprising at least one ribonucleotide residue. The term "ribonucleotide" is meant to include nucleotides with a hydroxyl group at the 2' position of a .beta.-D-ribo-furanose moiety. The term RNA includes, for example, double-stranded RNAs; single-stranded RNAs; and isolated RNAs such as partially purified RNA, essentially pure RNA, synthetic RNA, recombinantly produced RNA, as well as altered RNA that differ from naturally occurring RNA by the addition, deletion, substitution and/or alteration of one or more nucleotides. Such alterations can include addition of non-nucleotide material, such as to the end(s) of the siRNA or internally, for example at one or more nucleotides of the RNA. As disclosed in detail herein, nucleotides in the siRNA molecules of the instant invention can also comprise non-standard nucleotides, such as non-naturally occurring nucleotides or chemically synthesized nucleotides or deoxy-nucleotides. These altered RNAs can be referred to as analogs or analogs of naturally-occurring RNA.

The term "siRNA" refers to small interfering RNA; a siRNA is a double stranded RNA that "corresponds" to or matches a reference or target gene sequence. This matching need not be perfect so long as each strand of the siRNA is capable of binding to at least a portion of the target sequence. SiRNA can be used to inhibit gene expression, see for example Bass, 2001, Nature, 411, 428 429; Elbashir et al., 2001, Nature, 411, 494 498; and Zamore et al., Cell 101:25-33 (2000).

By "nucleic acid binding domain" (NABD) is meant to refer to a molecule, for example a protein, polypeptide, or peptide, that binds nucleic acids, such as DNA or RNA. The NABD may bind to single or double strands of RNA or DNA or mixed RNA/DNA hybrids. The nucleic acid binding domain may bind to a specific sequence or bind irrespective of the sequence.

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. In preferred embodiments, "nucleic acids" refer to RNA or DNA that are intended for internalization into a cell.

The term "pharmaceutically-acceptable excipient" as used herein means one or more compatible solid or liquid filler, diluents or encapsulating substances that are suitable for administration into a human.

Compositions

Cell specific antigens which are not naturally internalized are operative herein by incorporating an arginine-rich peptide within the ligand, an arginine-rich peptide attached to the cell surface receptor specific ligand, as detailed in U.S. Pat. Nos. 6,692,935 B1 or 6,294,353 B1. An arginine-rich peptide causes cellular internalization of a coupled molecule upon contact of the arginine-rich peptide with the cell membrane. Pentratin and transportan are appreciated to also be operative as vectors to induce cellular internalization of a coupled molecule through attachment to the cell surface receptor specific ligand as detailed in U.S. Pat. Nos. 6,692,935 B1 or 6,294,353 B1.

The functional RNA interference activity of interfering RNA transported into target cells while adsorbed to a fusion protein containing protamine as the RNA bonding protein and a Fab fragment specific for the HIV envelope protein gp160 has been demonstrated (Song et al. 2005). Similarly, functional RNA interference activity of interfering RNA transported into target cells as a cargo molecule attached to HIV-1 transactivator of transcription (TAT) peptide$_{47-57}$ has been demonstrated (Chiu Y-L et al. 2004). The functional RNA interference activity of interfering RNA transported into target cells as a cargo molecule attached to pentratin has also been demonstrated (Muratovska and Eccles 2004).

The dsRNA or shRNA oligonucleotide mediating RNA interference is delivered into the cell by internalization of the receptor.

DsRNA with siRNA sequences that are complementary to the nucleotide sequence of the target gene are prepared. The siRNA nucleotide sequence is obtained from the siRNA Selection Program, Whitehead Institute for Biomedical Research, Massachusetts Institute of Technology, Cambridge, Mass. after supplying the Accession Number or GI number from the National Center for Biotechnology Information website. The Genome Database provides the nucleic acid sequence link which is used as the National Center for Biotechnology Information accession number. Preparation of RNA to order is commercially available (Ambion Inc., Austin, Tex.; GenoMechanix, LLC, Gainesville, Fla.; and others). Determination of the appropriate sequences would be accomplished using the USPHS, NIH genetic sequence data bank. Alternatively, dsRNA containing appropriate siRNA sequences is ascertained using the strategy of Miyagishi and Taira (2003). DsRNA may be up to 800 base pairs long (Diallo M et al. 2003). The dsRNA optionally has a short hairpin structure (U.S. Patent Application Publication 2004/0058886). Commercially available RNAi designer algorithms also exist (Life Technologies, Grand Island, N.Y., USA).

Ligand-RNA binding fusion proteins are prepared using existing plasmid technology (Caron et al. 2004; He et al. 2004). RNA binding proteins illustratively include histone (Jacobs and Imani 1988), RDE-4 (Tabara et al. 2002; Parrish and Fire 2001), and protamine (Warrant and Kim 1978). RNA binding protein cDNA is determined using the Gene Bank database. For example, RDE-4 cDNA Gene Bank accession numbers are AY07926 and y1L832c2.3. RDE-4 initiates RNA interference by presenting dsRNA to Dicer (Tabara et al).

Additional dsRNA binding proteins (and their Accession numbers in parenthesis) include: PKR (AAA36409, AAA61926, Q03963), TRBP (P97473, AAA36765), PACT (AAC25672, AAA49947, NP_609646), Staufen (AAD17531, AAF98119, AAD17529, P25159), NFAR1 (AF167569), NFAR2 (AF167570, AAF31446, AAC71052, AAA19960, AAA19961, AAG22859), SPNR (AAK20832, AAF59924, A57284), RHA (CAA71668, AAC05725, AAF57297), NREBP (AAK07692, AAF23120, AAF54409, T33856), kanadaptin (AAK29177, AAB88191, AAF55582, NP_499172, NP_198700, BAB19354), HYL1 (NP_563850), hyponastic leaves (CAC05659, BAB00641), ADAR1 (AAB97118, P55266, AAK16102, AAB51687, AF051275), ADAR2 P78563, P51400, AAK17102, AAF63702), ADAR3 (AAF78094, AAB41862, AAF76894), TENR (XP_059592, CAA59168), RNaseIII (AAF80558, AAF59169, Z81070Q02555/S55784, P05797), and Dicer (BAA78691, AF408401, AAF56056, S44849, AAF03534, Q9884), RDE-4 (AY071926), FLJ20399 (NP_060273, BAB26260), CG1434 (AAF48360, EAA12065, CAA21662), CG13139 (XP_059208, XP_143416, XP_110450, AAF52926, EEA14824), DGCRK6 (BAB83032, XP_110167) CG1800 (AAF57175, EAA08039), FLJ20036 (AAH22270, XP_134159), MRP-L45 (BAB14234, XP_129893), CG2109 (AAF52025), CG12493 (NP_647927), CG10630 (AAF50777), CG17686 (AAD50502), T22A3.5 (CAB03384) and nameless Accession number EAA14308 as enumerated in Saunders and Barber 2003.

Alternatively, cell surface receptor specific ligands that are rich in arginine and tyrosine residues are constructed such that those residues are positioned to form hydrogen bonds with engineered RNA containing appropriately positioned guanine and uracil (Jones 2001). Additionally, the necessity and performance of an internalization moiety is determined in vitro.

The suitability of the resulting ligand-dsRNA as a substrate for Dicer is first determined in vitro using recombinant Dicer (Zhang H 2002, Provost 2002, Myers J W 2003). Optimal ligand molecule size and dsRNA length are thereby identified.

In one embodiment, the ligand-dsRNA binding molecule(s) illustratively include: a histone (Jacobs and Imani 1988), RDE-4 (Tabara et al. 2002; Parrish and Fire 2001), and protamine (Warrant and Kim 1978) in order to render the ligand-dsRNA hydrophilic. The histone with relatively lower RNA-histone binding affinity (Jacobs and Imani 1988) such as histone H1 (prepared as described by Kratzmeier M et al. 2000) is preferred. Alternatively, RDE-4 is used as prepared commercially (Qiagen, Valencia, Calif.) using RDE-4 cDNA (Gene Bank accession numbers AY07926 and y1L832c2.3). RDE-4 initiates RNA interference by presenting dsRNA to Dicer (Tabara et al).

Protamines are arginine-rich proteins. For example, protamine 1 contains 10 arginine residues between amino acid residue number 21 and residue number 35 (RSRRRRRRSCQTRRR) (Lee et al. 1987) (SEQ ID NO.: 12. Protamine binds to RNA (Warrant and Kim 1978).

In one aspect, the complex comprises one or more inhibitory nucleic acids and a targeting polypeptide, wherein the targeting polypeptide comprises of a cell surface receptor ligand. In certain examples, the targeting polypeptide further comprises a nucleic acid binding moiety.

A cell surface receptor specific ligand as used herein is defined as any molecule that binds to a cellular receptor or cell surface antigen. A ligand is then coupled to an appropriate inhibitory nucleic acid, e.g. a dsRNA binding protein. The ligand is a natural- or engineered-peptide or protein, such as is commercially available (Antibodies by Design, MorphoSys, Martinsried, Germany) (U.S. Pat. Nos. 5,514,548; 6,653,068 B2; 6,667,150 B1; 6,696,245; 6,753,136 B1; U.S. 2004/017291 A1).

Cytokines are small secreted proteins which mediate and regulate immunity, inflammation, and hematopoiesis. Cytokines are produced de novo in response to an immune stimulus. Cytokine is a general name; other names include lymphokine (cytokines made by lymphocytes), monokine (cytokines made by monocytes), chemokine (cytokines with chemotactic activities), and interleukin (cytokines made by one leukocyte and acting on other leukocytes). Cytokines may act on the cells that secrete them (autocrine action), on nearby cells (paracrine action), or in some instances on distant cells (endocrine action). Cytokines act on their target cells by binding specific membrane receptors. The receptors and their corresponding cytokines have been divided into several families based on their structure and activities. Hematopoietin family receptors are dimers or trimers with conserved cysteines in their extracellular domains and a conserved Trp-Ser-X-Trp-Ser sequence. Examples are receptors for IL-2 through IL-7 and GM-CSF. Interferon family receptors have the conserved cysteine residues but not the Trp-Ser-X-Trp-Ser sequence, and include the receptors for IFNa, IFNb, and IFNg. Tumor Necrosis Factor family receptors have four extracellular domains; they include receptors for soluble TNFa and TNFb as well as membrane-bound CD40 (important for B cell and macrophage activation) and Fas (which signals the cell to undergo apoptosis). Chemokine family receptors have seven transmembrane helices and interact with G protein. This family includes receptors for IL-8, MIP-1 and RANTES. Chemokine receptors CCR5 and CXCR4 are used by HIV to preferentially enter either macrophages or T cells.

Chemokines are a family of small cytokines that are secreted by cells. Chemokine receptors are G protein-coupled receptors containing 7 transmembrane domains that are found on the surface of leukocytes. Approximately 19 different chemokine receptors have been characterized to date, which are divided into four families depending on the type of chemokine they bind; CXCR that bind CXC chemokines, CCR that bind CC chemokines, CX3CR1 that binds the sole CX3C chemokine (CX3CL1), and XCR1 that binds the two XC chemokines (XCL1 and XCL2). They share many structural features; they are similar in size (with about 350 amino acids), have a short, acidic N-terminal end, seven helical transmembrane domains with three intracellular and three extracellular hydrophilic loops, and an intracellular C-terminus containing serine and threonine residues important for receptor regulation. The first two extracellular loops of chemokine receptors each have a conserved cysteine residue that allows formation of a disulfide bridge between these loops. G proteins are coupled to the C-terminal end of the chemokine receptor to allow intracellular signaling after receptor activation, while the N-terminal domain of the chemokine receptor determines ligand binding specificity.

Thus, in certain exemplary embodiments, the invention features complexes comprising one or more inhibitory nucleic acids and a targeting polypeptide, wherein the targeting polypeptide comprises a cell surface receptor ligand. The rageting polypeptide can comprise a chemokine. There are more than 50 chemokines known, and any may be suitable for use in the invention as claimed.

In certain examples, exemplary chemokines are CCL27 and CCL11.

As described above, in certain examples, the targeting polypeptide further comprises a nucleic acid binding moiety. The nucleic acid binding moiety is used to associate the targeting polypeptide and the inhibitory nucleic acid.

In certain examples, the nucleic acid binding domain comprises protamine, or a fragment thereof. Protamines are small, arginine-rich, nuclear proteins.

In other certain examples, the nucleic acid binding domain comprises a viral antigen. The viral antigen can be, in certain examples, a viral capsid antigen. Any viral capsid antigen is suitable for use in the invention, as long as it binds the inhibitory nucleic acid; however in certain examples, the viral capsid acid is selected from, but not limited to, gp120, gp160, gp41. In certain examples, the one or more inhibitory nucleic acids and the targeting polypeptide are joined by a linker.

The invention can also feature fusion molecules. A fusion molecule may comprise one or more inhibitory nucleic acids and a targeting polypeptide, wherein the targeting polypeptide comprises a cell surface receptor ligand. In certain examples, the targeting polypeptide can further comprise a linker.

Exemplary fusion molecules of the invention may comprise one or more inhibitory nucleic acids and a targeting polypeptide, wherein the targeting polypeptide further comprises a nucleic acid binding moiety, encoded by the nucleic acid sequence set forth as SEQ ID NO: 1 or SEQ ID NO: 3.

Exemplary fusion molecules of the invention may comprise a targeting polypeptide and a nucleic acid binding moiety, encoded by a polypeptide comprising the amino acid sequence of SEQ ID NO: 2, SEQ ID NO: 4, SEQ ID NO: 9, SEQ ID NO: 10 or SEQ ID NO: 11.

The linker may comprise a nucleic acid binding domain. As described, the nucleic acid binding domain can comprise protamine, or a fragment thereof. In certain cases, the protamine is human protamine. In other certain cases, the linker comprises a viral antigen, which, for example may be, but is not limited to, a viral antigen, for example a viral capsid antigen (e.g. gp120, gp160 or gp41).

Any linker can be used that connects or links the targeting polypeptide and the inhibitory nucleic acid. In certain examples, the targeting polypeptide can be linked to the inhibitory nucleic acid by simply a covalent bond that covalently bonds a hydrophilic polymer to a residue derived from the inhibitory nucleic acid.

The term "covalent attachment" means that the polypeptide and the non-polypeptide moiety, e.g. the nucleic acid moiety, are either directly covalently joined to one another, or else are indirectly covalently joined to one another through an intervening moiety or moieties, such as a linker, or a bridge, or a spacer, moiety or moieties. Preferably, a conjugated polypeptide is soluble at relevant concentrations and conditions, i.e. soluble in physiological fluids. There is no limit to the linker mediating the covalent bond between the hydrophilic polymer and the end group of the residue derived from the inhibitory nucleic acid. In certain cases, it is preferable that the linker be degradable on necessity under predetermined conditions. In other certain cases, the linker can be a polyalkylene glycol. For example, the linking moiety is polyethylene glycol (PEG). In other certain cases, the linker is a disulfide bond.

In one embodiment, the targeting polypeptide and the inhibitory polynucleotide are linked by the PEG linking moiety, such that the primary structure of the nucleic acid composition is a linear arrangement in which the targeting polypeptide is linked to a first terminus of the PEG linking moiety and the nucleic acid is linked to a second terminus of the PEG linking moiety.

U.S. Application 20070231392, incorporated by reference in its entirety herein, describes a non-viral carrier for nucleic acid delivery in vitro and in vivo. The polycation polymers described may form complexes with biomolecules and thus are useful as carriers for the delivery of biomolecules to cells. Examples of biomolecules that form complexes with the compound of the Formula I include nucleic acids, proteins, peptides, lipids, and carbohydrates. Examples of nucleic acids include DNA, single strand RNA, double strand RNA, ribozyme, DNA-RNA hybridizer, and antisense DNA, e.g., antisense oligo. Preferred nucleic acids are siRNA.

The functional RNA interference activity of RNAi transported into target cells while adsorbed to a complex as described herein containing protamine as the RNA bonding protein and a Fab fragment specific for the HIV envelope protein gp160 has been previously demonstrated (Song et al. 2005). Similarly, functional RNA interference activity of interfering RNA transported into target cells as a cargo molecule attached to HIV-1 transactivator of transcription (TAT) peptide 47-57 has been demonstrated (Chiu Y-L et al. 2004). The functional RNA interference activity of interfering RNA transported into target cells as a cargo molecule attached to pentratin has also been demonstrated (Muratovska and Eccles 2004).

In certain embodiments, the inhibitory nucleotides are delivered into the cell by internalization of the receptor.

In the event a targeted cell receptor is a unique receptor that is not naturally internalized, that receptor is nonetheless suitable as a target by incorporating an internalization moiety such as an arginine-rich membrane permeable peptide within the ligand or attaching to the ligand such as an arginine-rich membrane permeable peptide, pentratin, or transportan as detailed in U.S. Pat. Nos. 6,692,935 B1 or 6,294,353 B1.

RNA interference refers to the process of sequence-specific post-transcriptional gene silencing in animals mediated by short interfering RNAs (siRNAs) (Zamore et al., 2000, Cell, 101, 25-33; Fire et al., 1998, Nature, 391, 806; Hamilton et al., 1999, Science, 286, 950-951; Lin et al., 1999, Nature, 402, 128-129; Sharp, 1999, Genes & Dev., 13:139-141; and Strauss, 1999, Science, 286, 886). The corresponding process in plants (Heifetz et al., International PCT Publication No. WO 99/61631) is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., 1999, Trends Genet., 15, 358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. The presence of dsRNA in cells triggers the RNAi response through a mechanism that has yet to be fully characterized. This mechanism appears to be different from other known mechanisms involving double stranded RNA-specific ribonucleases, such as the interferon response that results from dsRNA-mediated activation of protein kinase PKR and 2',5'-oligoadenylate synthetase resulting in non-specific cleavage of mRNA by ribonuclease L (see for example U.S. Pat. Nos. 6,107,094; 5,898,031; Clemens et al., 1997, J. Interferon & Cytokine Res., 17, 503-524; Adah et al., 2001, Curr. Med. Chem., 8, 1189).

Haeberli et al. in U.S. Application No. 20070042983, incorporated by reference in its entirety herein, describe compounds, compositions, and methods useful for modulating gene expression using short interfering nucleic acid (siNA) molecules.

For example, an inhibitory nucleotide of the invention may comprise modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA. If the siNA molecule is single stranded, the percent modification can be based upon the total number of nucleotides present in the single stranded siNA molecules. Likewise, if the siNA molecule is double stranded, the percent modification can be based upon the total number of nucleotides present in the sense strand, antisense strand, or both the sense and antisense strands.

For example, an inhibitory nucleotide of the invention may comprise a double-stranded short interfering nucleic acid (siNA) molecule that down-regulates expression of a target gene or that directs cleavage of a target RNA. In one embodiment, the double stranded siNA molecule comprises one or more chemical modifications and each strand of the double-stranded siNA is about 21 nucleotides long. In one embodiment, the double-stranded siNA molecule does not contain any ribonucleotides. In another embodiment, the double-stranded siNA molecule comprises one or more ribonucleotides. In one embodiment, each strand of the double-stranded siNA molecule independently comprises about 15 to about 30 (e.g., about 15, 16, 17, 18, 19, 20, 21, 22, 23, 24, 25, 26, 27, 28, 29, or 30) nucleotides, wherein each strand comprises about 15 to about 30 (e.g., about 15, 16, 17, 18, 19, 20, 21, 22, 23, 24, 25, 26, 27, 28, 29, or 30) nucleotides that are complementary to the nucleotides of the other strand. In one embodiment, one of the strands of the double-stranded siNA molecule comprises a nucleotide sequence that is complementary to a nucleotide sequence or a portion thereof of the gene, and the second strand of the double-stranded siNA molecule comprises a nucleotide sequence substantially similar to the nucleotide sequence of the gene or a portion thereof.

For example, an inhibitory nucleotide of the invention may comprise a double-stranded short interfering nucleic acid (siNA) molecule that down-regulates expression of a target gene or that directs cleavage of a target RNA, comprising an antisense region, wherein the antisense region comprises a nucleotide sequence that is complementary to a nucleotide sequence of the gene or a portion thereof, and a sense region, wherein the sense region comprises a nucleotide sequence substantially similar to the nucleotide sequence of the gene or a portion thereof. In one embodiment, the antisense region and the sense region independently comprise about 15 to about 30 (e.g. about 15, 16, 17, 18, 19, 20, 21, 22, 23, 24, 25, 26, 27, 28, 29, or 30) nucleotides, wherein the antisense region comprises about 15 to about 30 (e.g. about 15, 16, 17, 18, 19, 20, 21, 22, 23, 24, 25, 26, 27, 28, 29, or 30) nucleotides that are complementary to nucleotides of the sense region.

For example, an inhibitory nucleotide of the invention may comprise a double-stranded short interfering nucleic acid (siNA) molecule that down-regulates expression of a target gene or that directs cleavage of a target RNA, comprising a sense region and an antisense region, wherein the antisense region comprises a nucleotide sequence that is complementary to a nucleotide sequence of RNA encoded by the gene or a portion thereof and the sense region comprises a nucleotide sequence that is complementary to the antisense region.

For example, an inhibitory nucleotide of the invention may comprise a double-stranded short interfering nucleic acid (siNA) molecule that down-regulates expression of a target gene or that directs cleavage of a target RNA, wherein the siNA molecule comprises about 15 to about 30 (e.g. about 15, 16, 17, 18, 19, 20, 21, 22, 23, 24, 25, 26, 27, 28, 29, or 30) base pairs, and wherein each strand of the siNA molecule comprises one or more chemical modifications. In another embodiment, one of the strands of the double-stranded siNA molecule comprises a nucleotide sequence that is complementary to a nucleotide sequence of a gene or a portion thereof, and the second strand of the double-stranded siNA molecule comprises a nucleotide sequence substantially similar to the nucleotide sequence or a portion thereof of the gene. In another embodiment, one of the strands of the double-stranded siNA molecule comprises a nucleotide sequence that is complementary to a nucleotide sequence of a gene or portion thereof, and the second strand of the double-stranded siNA molecule comprises a nucleotide sequence substantially similar to the nucleotide sequence or portion thereof of the gene. In another embodiment, each strand of the siNA molecule comprises about 15 to about 30 (e.g. about 15, 16, 17, 18, 19, 20, 21, 22, 23, 24, 25, 26, 27, 28, 29, or 30) nucleotides, and each strand comprises at least about 15 to about 30 (e.g. about 15, 16, 17, 18, 19, 20, 21, 22, 23, 24, 25, 26, 27, 28, 29, or 30) nucleotides that are complementary to the nucleotides of the other strand.

For example, an inhibitory nucleic acid of the invention may comprise a double-stranded short interfering nucleic acid (siNA) molecule that down-regulates expression of a target gene or that directs cleavage of a target RNA comprising a sense region and an antisense region, wherein the antisense region comprises a nucleotide sequence that is complementary to a nucleotide sequence of RNA encoded by the target gene or a portion thereof and the sense region comprises a nucleotide sequence that is complementary to the antisense region, and wherein the siNA molecule has one or more modified pyrimidine and/or purine nucleotides. In one embodiment, the pyrimidine nucleotides in the sense region are 2'-O-methylpyrimidine nucleotides or 2'-deoxy-2'-fluoro pyrimidine nucleotides and the purine nucleotides present in the sense region are 2'-deoxy purine nucleotides. In another embodiment, the pyrimidine nucleotides in the sense region are 2'-deoxy-2'-fluoro pyrimidine nucleotides and the purine nucleotides present in the sense region are 2'-O-methyl purine nucleotides. In another embodiment, the pyrimidine nucleotides in the sense region are 2'-deoxy-2'-fluoro pyrimidine nucleotides and the purine nucleotides present in the sense region are 2'-deoxy purine nucleotides. In one embodiment, the pyrimidine nucleotides in the antisense region are 2'-deoxy-2'-fluoro pyrimidine nucleotides and the purine nucleotides present in the antisense region are 2'-O-methyl or 2'-deoxy purine nucleotides. In another embodiment of any of the above-described siNA molecules, any nucleotides present in a non-complementary region of the sense strand (e.g. overhang region) are 2'-deoxy nucleotides.

For example, an inhibitory nucleic acid of the invention may comprise a double-stranded short interfering nucleic acid (siNA) molecule that down-regulates expression of a target gene or that directs cleavage of a target RNA, wherein the siNA molecule is assembled from two separate oligonucleotide fragments wherein one fragment comprises the sense region and the second fragment comprises the antisense region of the siNA molecule, and wherein the fragment comprising the sense region includes a terminal cap moiety at the 5'-end, the 3'-end, or both of the 5' and 3' ends of the fragment.

In certain examples, the inhibitory nucleic acid in the complex is a single stranded DNA or RNA, and may comprise two or more single stranded DNAs or RNAs. In other examples, the inhibitory nucleic acid is a double stranded DNA or RNA, and may comprise two or more double stranded DNAs or RNAs. Thus, the invention is suitable is certain examples for modulating the expression of more than one target gene in a subject or organism Exemplary complexes of the invention may comprise a targeting polypeptide and a nucleic acid binding moiety, wherein the targeting polypeptide and the nucleic acid binding domain are encoded by the nucleic acid sequence set forth as SEQ ID NO: 1 or SEQ ID NO: 3.

In other certain examples, it is possible that the nucleic acid binding moiety and the targeting polypeptide are separated by a spacer peptide. Exemplary spacer peptides may comprise SEQ ID NO: 5 (SDGGGSGGGGSLE) or SEQ ID NO: 6: (DGGGSGGGGSL). dsRNA with siRNA sequences that are complementary to the nucleotide sequence of the target gene are prepared. The siRNA nucleotide sequence is obtained from the siRNA Selection Program, Whitehead Institute for Biomedical Research, Massachusetts Institute of Technology, Cambridge, Mass. after supplying the Accession Number or GI number from the National Center for Biotechnology Information website. The Genome Database provides the nucleic acid sequence link which is used as the National Center for Biotechnology Information accession number. Preparation of RNA to order is commercially available (Ambion Inc., Austin, Tex.; GenoMechanix, LLC, Gainesville, Fla.; and others). Determination of the appropriate sequences would be accomplished using the USPHS, NTH genetic sequence data bank. Alternatively, dsRNA containing appropriate siRNA sequences is ascertained using the strategy of Miyagishi and Taira (2003). DsRNA may be up to 800 base pairs long (Diallo M et al. 2003). The dsRNA optionally has a short hairpin structure (U.S. Patent Application Publication 2004/0058886). Commercially available RNAi designer algorithms also exist.

Ligand-inhibitory nucleic acid binding complexes are prepared using existing plasmid technology (Caron et al. 2004; He et al. 2004). RNA binding proteins illustratively include histone (Jacobs and Imani 1988), RDE-4 (Tabara et al. 2002; Parrish and Fire 2001), and protamine (Warrant and Kim 1978). RNA binding protein cDNA is determined using the Gene Bank database. For example, RDE-4 cDNA Gene Bank accession numbers are AY07926 and y1L832c2.3. RDE-4 initiates RNA interference by presenting dsRNA to Dicer (Tabara et al).

In certain examples, the suitability of the resulting ligand-dsRNA as a substrate for Dicer can be first determined in vitro using recombinant Dicer (Zhang H 2002, Provost 2002, Myers J W 2003). Optimal ligand molecule size and dsRNA length are thereby identified.

The invention also features pharmaceutical compositions for treating the aforementioned disease or disorder in a subject comprising one or more inhibitory nucleic acids and a targeting polypeptide, wherein the targeting polypeptide consists of a cell surface receptor ligand, thereby treating or preventing a disease or disorder in a subject.

The pharmaceutical compositions, in certain embodiments, comprise treatment with an additional agent.

In other certain embodiment, the invention features a pharmaceutical composition for delivering one or more agents to a target cell comprising one or more inhibitory nucleic acids, wherein the one or more inhibitory nucleic acids are coupled to an agent, and a targeting polypeptide, wherein the targeting polypeptide consists of a cell surface receptor ligand, thereby treating or preventing a disease or disorder in a subject.

Methods

The compositions are provided herein based on utilizing a cell surface receptor targeting ligand, for example a chemokine, and a domain that binds an inhibitory oligonucleotide, to efficiently deliver the inhibitory oligonucleotide to the cell that expresses the cell surface receptor targeting ligand. The invention provides advantages over prior methods in providing highly efficient and targeted complexes.

Accordingly, the invention features methods of silencing, or knocking down, gene expression in a cell using the complexes as described herein In certain examples, the invention features methods of silencing gene expression in a cell comprising contacting the cell with a complex comprising one or more inhibitory nucleic acids that reduce the expression of one or more target genes and a targeting polypeptide, wherein the targeting polypeptide comprises a cell surface receptor ligand, thereby silencing gene expression in the cell.

The invention also features methods of delivering inhibitory RNA molecules into a cell, where the methods comprise contacting the cell with a complex comprising one or more double stranded RNAs and a targeting polypeptide, wherein the targeting polypeptide comprises a cell surface receptor ligand, thereby delivering inhibitory RNA molecules into a cell.

The invention also features methods of treating or preventing a disease or disorder in a subject by silencing gene expression comprising: contacting the cell with a complex comprising one or more inhibitory nucleic acids that reduce the expression of one or more target genes and a targeting polypeptide, wherein the targeting polypeptide consists of a cell surface receptor ligand, thereby treating or preventing a disease or disorder in a subject.

In certain examples, the methods are used to treat Waldenstrom's macroglobulinemia.

The invention also features methods of delivering one or more agents to a target cell comprising contacting the cell with a complex comprising one or more inhibitory nucleic acids that reduce the expression of one or more target genes, wherein the one or more inhibitory nucleic acids are coupled to an agent, and a targeting polypeptide, wherein the targeting polypeptide consists of a cell surface receptor ligand, thereby delivering the agent to a target cell.

In one embodiment, inhibitory nucleic acids, for example siNA molecules, of the invention are used as reagents in ex vivo applications. For example, siNA reagents are introduced into tissue or cells that are transplanted into a subject for therapeutic effect. The cells and/or tissue can be derived from an organism or subject that later receives the explant, or can be derived from another organism or subject prior to transplantation. The siNA molecules can be used to modulate the expression of one or more target genes in the cells or tissue, such that the cells or tissue obtain a desired phenotype or are able to perform a function when transplanted in vivo. In one embodiment, certain target cells from a patient are extracted. These extracted cells are contacted with siNAs targeting a specific nucleotide sequence within the cells under conditions suitable for uptake of the siNAs by these cells (e.g. using delivery reagents such as cationic lipids, liposomes and the like or using techniques such as electroporation to facilitate the delivery of siNAs into cells). The cells are then reintroduced back into the same patient or other patients. Thus, in one embodiment, the invention features a method of modulating the expression of a target gene in a tissue explant comprising: (a) synthesizing a complex of the invention, e.g. a complex comprising one or more inhibitory nucleic acids and a targeting polypeptide, wherein the targeting polypeptide consists of a cell surface receptor ligand, and wherein one of the siNA strands comprises a sequence complementary to RNA of the target gene; and (b) introducing the complex into a cell of the tissue explant derived from a particular organism under conditions suitable to modulate the expression of the target gene in the tissue explant. In another embodiment, the method further comprises introducing the tissue explant back into the organism the tissue was derived from or into another organism under conditions suitable to modulate the expression of the target gene in that organism.

In certain examples, the cell is a cultured cell. In other certain examples, the cell is part of a subject animal.

The cell can be a malignant cell.

The subject can be a human. In certain embodiments, the subject is suffering from Waldenstrom's macroglobulinemia Patient Monitoring The disease state or treatment of a patient having a disease or disorder, for example Waldenstrom's macroglobulinemia, can be monitored using the methods and compositions of the invention.

In one embodiment, the tumor progression of a patient can be monitored using the methods and compositions of the invention. Such monitoring may be useful, for example, in assessing the efficacy of a particular drug in a patient. For examples, therapeutics that alter the expression of a target polypeptide that is overexpressed in a neoplasia are taken as particularly useful in the invention.

Kits

The invention also provides kits for treating or preventing a disease or disorder in a subject by silencing gene expression. In preferred examples, the kits provide one or more inhibitory nucleic acids and a targeting polypeptide, wherein the targeting polypeptide consists of a cell surface receptor ligand. In other preferred examples, the kits comprise the fusion molecule as described herein, and instructions for use.

In other embodiments, the kit comprises a sterile container which contains the inhibitory nucleotide, the targeting polypeptide and optionally additional agents; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the inhibitory nucleotides and additional agents as described herein and their use in the methods as described herein. Preferably, the kit further comprises any one or more of the reagents described in the diagnostic assays described herein. In other embodiments, the instructions include at least one of the following: description of the inhibitory nucleotides; methods for using the enclosed materials for the diagnostic and prognostic methods as described herein; precautions; warnings; indications; clinical or research studies; and/or references. The instructions may be printed directly on the container (when present), or as a label applied to the container, or as a separate sheet, pamphlet, card, or folder supplied in or with the container.

EXAMPLES

Example 1

The invention features, generally, complexes comprising one or more inhibitory nucleic acids and a targeting polypeptide, where the targeting polypeptide consists of a cell surface receptor ligand.

In other examples, the complexes are modified. For example, the RNA binding portion of the complex is modified by reducing its size and/or increasing affinity. As described herein, His residues may be included in the constructs for analytical use and protein purification purposes; however these His residues are not necessary. Accordingly, certain constructs do not have His-tag. The exclusion of the His tag allows increased RNA binding affinity of the complex.

Example 2

Experiments were also performed with antisense oligomers to interleukin-10 (IL-10) as part of complexes as described herein. In the same type of experiments as described above, it was found that antisense oligomers to IL-10 in a complex as described herein are effective to inhibit IL-10 expression.

Example 3

Preparation of the ligand-histone-dsRNA complex is accomplished as described by (Yoshikawa et al. 2001). Complexes of ligand-lysine rich histone, the histone containing 24.7% (w/w) lysine and 1.9% arginine (w/w), with dsRNA is prepared by gentle dilution from a 2 M NaCl solution. Ligand-histone and dsRNA are dissolved in 2 M NaCl/10 mM Tris/HCl, pH 7.4, in which the charge ratio of dsRNA:histone (−/+) is adjusted to 1.0. Then the 2 M NaCl solution is slowly dispersed in distilled water in a glass vessel to obtain 0.2 M and 50 mM NaCl solutions. The final volume is 200 μL and final dsRNA concentration is 0.75 μM in nucleotide units.

Preparation of the ligand-RDE-4-dsRNA-complex is accomplished as described by (Johnston et al. 1992), for the conserved double-stranded RNA binding domain which RDE-4 contains. Ligand-RDE-4 binding to dsRNA to is accomplished in 50 mM NaCl/10 mM $MgCl_2$/10 mM Hepes, pH 8/0.1 mM EDTA/1 mM dithiothreitol/2.5% (wt/vol) non-fat dry milk.

Preparation of the ligand-protamine-dsRNA complex is accomplished as described by (Warrant and Kim 1978). The ligand-protamine (human recombinant protamine 1, Abnova Corporation, Taiwan) and dsRNA at a molar ratio of 1:4 are placed in a buffered solution containing 40 mM Na cacodylate, 40 mM $MgCl_2$, 3 mM spermine HCl at pH 6.0 (Warrant and Kim 1978). The solution is incubated at 4° C.-6° C. for several days. Alternatively, the ligand-protamine-dsRNA complex is prepared as described by Song et al. 2005. The siRNA (300 nM) is mixed with the ligand-protamine protein at a molar ratio of 6:1 in phosphate buffered saline for 30 minutes at 4° C.

The constructed ligand-RNA binding protein-dsRNA complex is then administered parenterally and binds to its target cell via its receptor. The constructed ligand-RNA binding protein-dsRNA complex is then internalized and the dsRNA is hydrolyzed by Dicer thereby releasing siRNA for gene silencing.

A therapeutic protein operative in certain embodiments of the present invention is a mutant form of a native protein. Mutants operative herein illustratively include amino acid substitutions relative to amino acid sequences detailed herein. It is further appreciated that mutation of the conserved amino acid at any particular site is preferably mutated to glycine or alanine. It is further appreciated that mutation to any neutrally charged, charged, hydrophobic, hydrophilic, synthetic, non-natural, non-human, or other amino acid is similarly operable.

Modifications and changes are optionally made in the structure (primary, secondary, or tertiary) of the therapeutic protein which are encompassed within the inventive compound that may or may not result in a molecule having similar characteristics to the exemplary polypeptides disclosed herein. It is appreciated that changes in conserved amino acid bases are most likely to impact the activity of the resultant protein. However, it is further appreciated that changes in amino acids operable for receptor interaction, resistance or promotion of protein degradation, intracellular or extracellular trafficking, secretion, protein-protein interaction, post-translational modification such as glycosylation, phosphorylation, sulfonation, and the like, may result in increased or decreased activity of an inventive compound while retaining some ability to alter or maintain a physiological activity. Certain amino acid substitutions for other amino acids in a sequence are known to occur without appreciable loss of activity.

In making such changes, the hydropathic index of amino acids are considered. According to the present invention, certain amino acids can be substituted for other amino acids having a similar hydropathic index and still result in a polypeptide with similar biological activity. Each amino acid is assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Without intending to be limited to a particular theory, it is believed that the relative hydropathic character of the amino acid determines the secondary structure of the resultant polypeptide, which in turn defines the interaction of the polypeptide with other molecules. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

Example 4

Waldenström's macroglobulinemia remains an incurable and fatal disease. The manifestations of this disease that are due to high concentrations of monoclonal IgM are hyperviscosity and systemic amyloidosis which may result in death.

CCR10 and CCR3 are a cell surface receptors found on macroglobulinemia plasma cells (Homey et al 2000, Kitaura 1996)). Ligation of CCR10 with CCL27 or CCR3 with CCL11 results in internalization of the ligands.

CCL27-protamine fusion protein or CCL11-protamine fusion protein is prepared as described (Arya 2016 1996, pp 456-493). The CCL27-protamine fusion protein or CCL11-protamine fusion protein is adsorbed to dsRNA containing a siRNA sequence that is complementary to a portion of the nucleotide sequence of the rearranged heavy chain of IgM (Yoshikawa et al. 2001, Song et al. 2005). The siRNA sequences provided by Invitrogen BLOCK-iT™ RNAi Designer for optimal suppression of IgM mu chain are 1. AJ294734_stealth_530: Sense Sequence (SEQ ID. NO.: 13) and Antisense Sequence UUGAUGGUCAGUGUGCUGGUCACCU (SEQ ID. NO.: 14).; and 2. AJ294734_stealth_864 Sense Sequence CAGCAUCUGCGAGGAUGACUGGAAU (SEQ ID. NO.: 15) and Antisense Sequence AUUCCAGUCAUCCUCGCAGAUGCUG (SEQ ID. NO.: 16). The siRNA is then incorporated into dsRNA. Varying doses ranging from 0.4 to 15 grams of the CCL27-protamine fusion protein or CCL11-protamine fusion protein dsRNA are administered depending upon response. Effective doses of CCL27-protamine fusion protein or CCL11-protamine fusion protein dsRNA need to be administered at intervals ranging from one day to several days in order to maintain suppression of IgM production. Because the half life of IgM is up to approximately 8 days, the circulating concentration of the macroglobulinemia IgM will decrease gradually over several weeks. Suppression of the IgM immunoglobulin class will allow maintenance of IgG mediated immunity because the IgG concentration is not reduced. Improvement and/or prevention aspects of the disease which are consequences of high concentrations of the macroglobulinemia protein occur gradually as the concentration of that protein decreases. A direct effect of high concentrations of macroglobulinemia protein is hyperviscosity. This morbid effect of Waldenstrom's macroglobulinemia is inhibited.

The CCL27-protamine fusion protein or CCL11-protamine fusion protein dsRNA containing the above described siRNA then binds to CCR10 or CCR3, respectively, on the surfaces of the subject's plasma cells. Following internalization, Dicer hydrolyzes the dsRNA into siRNA which then interrupts the malignant plasma cell production of IgM macroglobulinemia protein.

Example 5

Design of the CCL27-protamine fusion protein. The cDNA sequence for hCCL27-protamine is provided below (SEQ ID. NO.: 17):

```
ATGGTCCTACTGCCACCCAGCACTGCCTGCTGTACTCAGCTCTACCGAAA
GCCACTCTCAGACAAGCTACTGAGGAAGGTCATCCAGGTGGAACTGCAGG
AGGCTGACGGGGACTGTCACCTCCGGGCTTTCGTGCTTCACCTGGCTCAA
CGCAGCATCTGCATCCACCCCCAGAACCCCAGCCTGTCACAGTGGTTTGA
GCACCAAGAGAGAAAGCTCCATGGGACTCTGCCCAAGCTGAATTTTGGGA
TGCTAAGGAAAATGGGCGGTGGTGGCTCTGGCGGTGAAGCTTCCCTCGAC
```

-continued

CGCAGCCAGAGCCGTAGCCGTTATTACCGCCAGCGCCAACGTTCTCGCCG

CCGTCGCCGTCGCAGCTAA

The corresponding amino acid sequence generated therefrom is provided below (SEQ ID. NO.: 18):

MVLLPPSTACCTQLYRKPLSDKLLRKVIQVELQEADGDCHLRAFVLHLAQ

RSICIHPQNPSLSQWFEHQERKLHGTLPKLNFGMLRKMGGGGSGGEASLD

RSQSRSRYYRQRQRSRRRRRRS

A predicted cDNA sequence, optimized for appropriate codon usage is created, and then synthesized by Life Technologies (Carlsbad, Calif., USA).

Example 6

Design of the CCL11-protamine fusion protein.

The cDNA sequences for hCCL27-protamine are provided below (SEQ ID. NO.: 19:

ATGGGGCCAGCTTCTGTCCCAACCACCTGCTGCTTTAACCTGGCCAATAG

GAAGATACCCCTTCAGCGACTAGAGAGCTACAGGAGAATCACCAGTGGCA

AATGTCCCCAGAAAGCTGTGATCTTCAAGACCAAACTGGCCAAGGATATC

TGTGCCGACCCCAAGAAGAAGTGGGTGCAGGATTCCATGAAGTATCTGGA

CCAAAAATCTCCAACTCCAAAGCCAGGTGGTGGCTCTGGCGGTGAAGCTT

CCCTCGACCGCAGCCAGAGCCGTAGCCGTTATTACCGCCAGCGCCAACGT

TCTCGCCGCCGTCGCCGTCGCAGCTAA

The corresponding amino acid sequence generated therefrom is provided below (SEQ ID. NO.: 20):

MGPASVPTTCCFNLANRKIPLQRLESYRRITSGKCPQKAVIFKTKLAKDI

CADPKKKWVQDSMKYLDQKSPTPKPGGGSGGEASLDRSQSRSRYYRQRQR

SRRRRRRS

A predicted cDNA sequence, optimized for appropriate codon usage is created, and then synthesized by Life Technologies (Carlsbad, Calif., USA).

Example 7

The process of Example 4 is repeated with CCL28 in place of CCL11 or CCL27 as part of a protamine fusion protein. The amino acid sequence of CCL28 is provided below and include 184 residues (SEQ ID. NO.: 21):

MQQRGLAIVA LAVCAALHAS EAILPIASSC CTEVSHHISR

RLLERVNMCR IQRADGDCDL AAVILHVKRR RICVSPHNHT

VKQWMKVQAA KKNGKGNVCH RKKHHGKRNS NRAHQGKHET

YGHKTPYGGG SGGEASLDRS QSRSRYYRQR QRSRRRRRRS

LERGSAEEQK LISEEDLAHH HHHH

REFERENCES

Almeida J, Orfao A, Mateo G, Ocqueteau M, Garcia-Sanz R, Moro M J, Hernandez J, Ortega F, Borrego D, Barez A, Mejida M, San Miguel J F. Immunophenotypic and DNA content characteristics of plasma cells in multiple myeloma and monoclonal gammopathy of undetermined significance. Path Biol 1999; 47:119-127.

Anderson D C, Nichols E, Manger R, Woodle D, Barry M, Fritzberg A R. Tumor cell retention of antibody Fab fragments is enhanced by an attached HIV TAT protein-derived peptide. Biochem Biophys Res Commun 1993; 194:876-884.

Bauer S, Abdgawad M, Gunnarsson L, Segelmark M, Tapper H, and Hellmark T. Proteinase 3 and CD177 are expressed on the plasma membrane of the same subset of neutrophils. J. Leukoc. Biol. 2007; 81:458-464

Becker J M. Allergic Rhinitis, in In eMedicine, eds: Park C L, Mary L Windle M L, Georgitis J W, Pallares D, M D, Ballow M. 2004.

Brake M, Somers D. IgA Nephropathy in eMedicine, eds: Sondheimer J H, Talavera, F, Thomas C, Schmidt R J, Vecihi Batuman V. 2003.

Caron N J, Quenneville S P, Tremblay J P. Endosome disruption enhances functional nuclear delivery of Tat-fusion proteins. Biochem Biophys Res Commun 2004; 319:12-20.

CellSensor CRE-bla Jurkat Cell-based Assay Protocol, Catalogue number K1134 (K1079), Invitrogen Corporation, Carlsbad, Calif.

Chiu Y-L, Ali A, Chu C-y, Cao H, Rana T M. Visualizing a correlation between siRNA localization, cellular uptake, and RNAi in living cells. Chem Biol 2004; 11:1165-1175.

Diallo M, Arenz C, Schmitz K, Sandhoff K, Scheppers U. Long endogenous dsRNAs can induce complete gene silencing in mammalian cells and primary cultures. Oligonucleotides 2003; 13:381-392.

Ulf Forssmann, Carsten Stoetzer, Michael Stephan, Carsten Kruschinski, Thomas Skripuletz, Jutta Schade, Andreas Schmiedl, Reinhard Pabst, Leona Wagner, Torsten Hoffmann, Astrid Kehlen, Sylvia E. Escher, Wolf-Georg Forssmann, Jörn Elsner and Stephan von Horsten Inhibition of CD26/Dipeptidyl Peptidase IV Enhances CCL11/Eotaxin-Mediated Recruitment of Eosinophils In Vivo J Immunol Jul. 15, 2008, 181 (2) 1120-1127.

Funaro A, Reinis M, Trubiani O, Santi S, Di Primio R, Malavasi F. CD38 functions are regulated through an internalization step. J Immunol 1998; 160:2238-2247.

Futaki S, Goto S, Sugiura Y. Membrane permeability commonly shared among arginine-rich peptides. J Mol Recognit 2003; 16:260-264.

Grethlein S. Multiple Myeloma. In eMedicine, eds: Krishnan K, Talavera F, Guthrie T H, McKenna Rajalaxmi, Besa E C 2003.

He D, Yang H, Lin Q, Huang H. Arg9-peptide facilitates the internalization of an anti-CEA imunotoxin and potentiates its specific cytotoxity to target cells. Int J Biochem Cell Biol 2005; 37:192-205.

Hermanson G T. Bioconjugate Techniques. Academic Press, San Diego, Calif. 1996.

Homey et al. The orphan chemokine receptor G protein-coupled receptor-2 (GPR-2, CCR10) binds the skin-associated chemokine CCL27 (CTACK/ALP/ILC). J. Immunol: 164:3465-3470, 2000.

Hutvagner G, Zamore P D. A microRNA in a multiple-turnover RNAi enzyme complex. Nature 2002; 297:2056-2060.

Hutvagner G, Zamore P D. RNAi: nature abhors a double-strand. Curr Opinion in Genetics and Development 2002; 12:225-232.

Jacobs B L, Imani F. Histone proteins inhibit activation of the interferon-induced protein kinase by binding to double-stranded RNA. J Interferon Res 1988; 8:821-830.

Graham Jarmin, Wendy Lambie, Janet W. Baird and Gerard J. Andreas Gortz, Robert J. B. Nibbs, Pauline McLean, Function Novel Modes of Intracrine and Paracrine The Chemokine ESkine/CCL27 Displays J Immunol 2002; 169:1387-1394.

Jo D, Nashabi A, Doxee C, Lin Q, Unutmaz D, Chen J, Ruley H E. Epigenetic regulation of gene structure and function with a cell-permeable Cre recombinase. Nature Biotechnology 2001; 19:929-933.

Jones S, Daley T A, Luscombe N M, Berman H M, Thornton J M. Protein-RNA interactions: a structural analysis. Nucl Acids Res 2001; 29:943-954.

Kabat E A, Wu T T, Perry H M, Gottesman K S, Foeller C. Sequences of Proteins of Immunological Interest. Fifth Edition. Tabulation and Analysis of Amino Acid and Nucleic Acid Sequences of Precursors, V-Regions, C-Regions, J-Chain, T-Cell Receptors for Antigen, T-Cell Surface Antigens, $\beta_2$-Microglobulins, Major Histocompatibility Antigens, Thy-1, Complement, C-Reactive Protein, Thymopoietin, Integrins, Post-gamma Globulin, $\alpha_2$-Macroglobulins, and other Related Proteins. 1991. NIH Publication Number 91-3242.

Kitaura M, Nakajima T, Imai T, Harada S, Combadiere C, Tiffany H L, Murphy P M, Yoshie O (March 1996). "Molecular cloning of human eotaxin, an eosinophil-selective CC chemokine, and identification of a specific eosinophil eotaxin receptor, CC chemokine receptor 3". *The Journal of Biological Chemistry.* 271 (13): 7725-30.

Kratzmeier M, Albig W, Hanecke K, Doenecke D. Rapid dephosphorylation of H1 histones after apoptosis induction. J Biol Chem. 2000; 275:30478-30486.

Lee C-H, Hoyer-Fender S, Engel W. The nucleotide sequence of a human protamine 1 cDNA. Nucleic Acids Research 1987; 15:7639.

Mie M, Takahashi F, Funabashi H, Yanagida Y, Aizawa M, Kobatake E. Intracellular delivery of antibodies using TAT fusion protein A. Biochem Biophys Res Commun 2003; 310:730-734.

Miller V M, Xia H, Marrs G L, Gouvion C M, Lee G, Davidson B L, Paulson H L. Allele-specific silencing of dominant disease genes. Proc Natl Acad Sci USA 2003; 100:7195-7200.

Miyagishi M, Taira K. Strategies for generation of an siRNA expression library directed against the human genome. Oligonucleotides 2003; 13:325-333.

Muratovska A, Eccles M R. Conjugate for efficient delivery of short interfering RNA (siRNA) into mammalian cells. FEBS Letters 2004; 558:63-68.

Myers J W, Jones J T, Meyer T, Ferrell J E Jr. Recombinant Dicer efficiently converts large dsRNAs into siRNAs suitable for gene silencing. Nature Biotechnology 2003; 21:324-328.

Pan J, Kunkel E J, Gosslar U, Lazarus N, Langdon P, Broadwell K, Vierra M A, Genovese M C, Butcher E C, Soler D. Cutting Edge: A Novel Chemokine Ligand for CCR10 And CCR3 Expressed by Epithelial Cells in Mucosal Tissuesl, *J Immunol* 2000; 165:2943-2949. Parrish S, Fire A. Distinct roles for RDE-1 and RDE-4 during RNA interference in *Caenorhabditis elegans*. RNA 2001; 7:1397-1402.

Peitz M, Pfannkuche K, Rajewsky K, Edenhofer F. Ability of the hydrophobic FGF and basic TAT peptides to promote cellular uptake of the recombinant Cre recombinase: A tool for efficient genetic engineering of mammalian genomes. Proc Natl Acad Sci USAS 2002; 99:4489-4494.

Pfister M, Ogilvie A, da Silva C P, Grahnert A, Guse A H, Hauschildt S. NAD degradation and regulation of CD38 expression by human monocytes/macrophages. Eur J Biochem 2001; 268:5601-5608.

Provost P, Dishart D, Doucer J, Frendewey D, Samuelsson B, Radmark O. Ribonuclease activity and RNA binding of recombinant human Dicer. EMBO J 2002; 21:5864-5874.

Scott L M, Tong W, Levine R L, Scott M A, Beer P A, Stratton M R, Futreal P A, Erber W N, McMullin M F, Harrison C N, Warren A J, Gilliland D G, Lodish H F, Green A R. JAK2 exon 12 mutations in polycythemia vera and idiopathic erythrocytosis. N Engl J Med. 2007; 356:459-68.

St. Johnston D, Brown N H, Gall J G, Jantsch M. A conserved double-stranded RNA-binding domain. Proc Natl Acad Sci USA 1992; 89:10979-10983.

Saunders L A, Barber G N. The dsRNA binding protein family: critical roles, diverse cellular functions. FASEB J 2003; 17:961-983.

Siraganian R P. Biochemical events in basophil or mast cell activation and mediator release. Chapter 16 pp 204-227 in Allergy Principles and Practice, $5^{th}$ edition, eds E Middleton, Jr, C E Reed, E F Ellis, N F Adkinson, Jr, J W Yunginger W W Busse. Mosby, St. Louis, 1998.

Song E, Zhu P, Lee S-K, Chowdury D, Kussman S, Dykxhoorn D M, Feng Y, Palliser D, Weiner D B, Shankar P, Marasco W A, Lieberman J. Antibody mediated in vivo delivery of small interfering RNAs via cell-surface receptors. Nature Biotechnology (epublication): 22 May 2005; doi:10.1038/nbt1101; (paper publication): 2005; 23:709-717.

Soomets U, Lindgren M, Gallet X, Hallbrink M, Elmquist A, Balaspiri L, Zorka M, Pooga M, Brasseur R, Langel U. Deletion analogues of transportan. Biochem Biophys Acta 2000; 1467:165-176.

Stura E A, Fieser G G, Wilson I A. Crystallization of antibodies and antibody-antigen complexes. Immunomethods 1993; 3:164-179.

Tabara H, Yigit E, Siomi H, Mello C C. The dsRNA binding protein RDE-4 interacts with RDE-1, DCR-1 and a DexH-Box helicase to direct RNAi in *C. elegans*. Cell 2002; 109:861-871.

Temerinac S., Klippel S, Strunck E, Roder S, Lübbert M, Lange S, Azemar M, Meinhardt G, Schaefer H, and Pahl H, Cloning of PRV-1, a novel member of the uPAR receptor superfamily, which is overexpressed in polycythemia rubra vera. Blood 2000; 95: 2569-2576.

van Koningsbruggen S, de Haard H, de Kievit P, Dirks R W, van Remoortere A, Groot A J, van Engelen B G, den Dunnen J T, Verrips C T, Frants R R, van der Maarel S M. Llama-derived phage display antibodies in the dissection of the human disease oculopharyngeal muscular dystrophy. J Immunol Methods 2003; 279: 149-161.

Warrant R W, Kim S-H. $\alpha$-Helix-double helix interaction shown in the structure of a protamine-transfer RNA complex and a nucleoprotamine model. Nature 1978; 271:130-135.

Waterhouse P M, Wang M-B, Lough T. Gene silencing as an adaptive defense against viruses. Nature 2001; 411:834-842.

Yaneva J, Leuba S H, van Holde K, Zlatanova J. The major chromatin protein histone H1 binds preferentially to cis-platinum-damaged DNA. Proc Natl Acad Sci USA 1997; 94:13448-13451.

Yoshikawa Y, Velichko Y S, Ichiba Y, Yoshikawa K. Self-assembled pearling structure of long duplex DNA with histone H1. Eur J Biochem 2001; 268:2593-2599.

Zhang H, Kolb F A, Brondini V, Billy E, Filipowicz W. Human Dicer preferentially cleaves dsRNAs at their termini without a requirement for ATP. EMBO J 2002; 21:5875-5885.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A fusion molecule comprising one or more inhibitory nucleic acids, a targeting polypeptide, and a nucleic acid binding moiety, wherein said targeting polypeptide is the amino acid sequence of SEQ ID NO: 21.

2. A fusion molecule comprising one or more inhibitory nucleic acids, a targeting polypeptide, and a nucleic acid binding moiety binding a double-stranded RNA or a small hairpin RNA, wherein said targeting polypeptide consists of the amino acid sequence of SEQ ID NO: 21 or a fragment thereof having like targeting, said nucleic acid binding moiety is selected from the group consisting of: histone, protamine, cysteine-less human protamine 1, and wherein said nucleic acid binding moiety is fused with an internalization moiety.

3. The fusion molecule of claim 2, wherein said double-stranded RNA is complementary to a nucleotide sequence of a target gene and said targeting polypeptide is plasma cell binding.

4. The fusion molecule of claim 2 wherein said internalization moiety has a covalent bond to said nucleic acid binding moiety.

5. The fusion molecule of claim 2 wherein said internalization moiety is selected from the group of membrane-permeable arginine-rich peptides, pentratin, transportan, and transportan deletion analogs.

6. The fusion protein of claim 2 wherein said double-stranded RNA or said small hairpin RNA sequence is complementary to an IgM mu chain sequence.

* * * * *